US011857398B2

(12) United States Patent
Weber et al.

(10) Patent No.: US 11,857,398 B2
(45) Date of Patent: Jan. 2, 2024

(54) APPARATUS FOR AND METHOD OF SHAPING AND APPLYING A SEGMENT TO A MOVING WEB WITH SIDE SHIFTING PUCKS

(71) Applicant: Kimberly-Clark Worldwide, Inc., Neenah, WI (US)

(72) Inventors: Paul A. Weber, Menasha, WI (US); Michael L. Lohoff, Oshkosh, WI (US); Matthew J. Maigatter, Menasha, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 18/024,921

(22) PCT Filed: Oct. 6, 2020

(86) PCT No.: PCT/US2020/054425
§ 371 (c)(1),
(2) Date: Mar. 6, 2023

(87) PCT Pub. No.: WO2022/075978
PCT Pub. Date: Apr. 14, 2022

(65) Prior Publication Data
US 2023/0240903 A1 Aug. 3, 2023

(51) Int. Cl.
*A61F 13/15* (2006.01)

(52) U.S. Cl.
CPC .. *A61F 13/15699* (2013.01); *A61F 13/15707* (2013.01); *A61F 13/15756* (2013.01); *A61F 13/15764* (2013.01)

(58) Field of Classification Search
CPC .......... A61F 13/15699; A61F 13/15707; A61F 13/15756; A61F 13/15764
(Continued)

(56) References Cited

U.S. PATENT DOCUMENTS 4,523,671 A * 6/1985 Campbell ............ B65G 47/082
198/441
6,139,004 A 10/2000 Couillard et al.
(Continued)

FOREIGN PATENT DOCUMENTS

| DE | 60132767 T2 * | 2/2009 | ....... A61F 13/15699 |
| EP | 1961403 A2 | 8/2008 | |
| WO | 2008105984 A2 | 9/2008 | |

OTHER PUBLICATIONS

Coenen DE-60132767-T2, A61F13/15699.*
(Continued)

*Primary Examiner* — Gene O Crawford
*Assistant Examiner* — Lester Rushin, III
(74) *Attorney, Agent, or Firm* — Armstrong Teasdale LLP

(57) ABSTRACT

An apparatus for conveying and applying a discrete part to a substrate includes a plurality of transfer puck assemblies, a drive assembly, and a translation mechanism. The plurality of transfer puck assemblies is adapted to convey the discrete part to the substrate, and each transfer puck assembly includes at least one puck segment. The drive assembly is configured to rotate each transfer puck assembly about a drive axis. The translation mechanism is configured to translate the at least one puck segment in an axial direction as the plurality of transfer puck assemblies are being rotated about the drive axis to move the discrete part to a profiled configuration prior to application of the profiled discrete part to the substrate.

20 Claims, 24 Drawing Sheets

(58) Field of Classification Search
USPC ..... 198/418, 339.1, 345.1, 345.11, 373, 374, 198/375
See application file for complete search history.

(56) References Cited

U.S. PATENT DOCUMENTS

| | | | |
|---|---|---|---|
| 6,540,857 B1 | 4/2003 | Coenen et al. | |
| 7,335,150 B2* | 2/2008 | Coenen | A61F 13/15804 493/359 |
| 9,221,195 B2 | 12/2015 | Hargett et al. | |
| 9,266,314 B2 | 2/2016 | Findley et al. | |
| 9,433,538 B2 | 9/2016 | Pagel et al. | |
| 9,737,442 B2 | 8/2017 | Findley et al. | |
| 9,821,542 B2 | 11/2017 | Bruce et al. | |
| 9,862,112 B2 | 1/2018 | McCabe et al. | |
| 9,950,439 B2 | 4/2018 | McCabe et al. | |
| 11,712,376 B2* | 8/2023 | Ninomiya | B32B 37/00 604/385.16 |
| 2005/0133150 A1 | 6/2005 | Vaneperen et al. | |
| 2007/0142194 A1* | 6/2007 | Coenen | A61F 13/15707 493/405 |
| 2010/0154970 A1 | 6/2010 | Lohoff | |
| 2013/0035222 A1 | 2/2013 | Andrews et al. | |
| 2013/0152360 A1 | 6/2013 | Schoultz et al. | |
| 2016/0030252 A1 | 2/2016 | Sayaovong et al. | |
| 2019/0328591 A1* | 10/2019 | Heinz | B65B 35/24 |
| 2023/0233382 A1* | 7/2023 | Umebayashi | A61F 13/15747 156/192 |
| 2023/0233384 A1* | 7/2023 | Dria | A61F 13/53 604/365 |

OTHER PUBLICATIONS

Joa's Manufacturing Processes, Curt G. Joa, Inc., May 15, 2018; 12 pp.
PCT International Search Report and Written Opinion for Patent Application PCT/US2020/054425 dated Jun. 29, 2021; 11 pp.

* cited by examiner

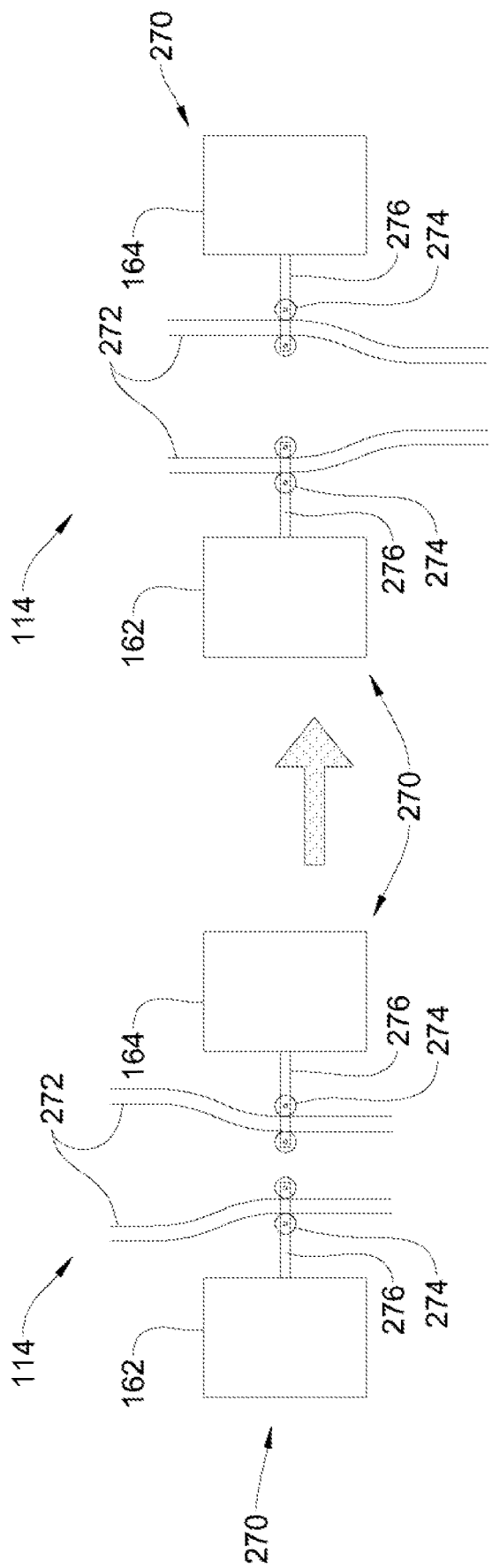

APPARATUS FOR AND METHOD OF SHAPING AND APPLYING A SEGMENT TO A MOVING WEB WITH SIDE SHIFTING PUCKS

CROSS-REFERENCE TO RELATED APPLICATION

This application is a U.S. National Phase Application of PCT/US2020/054425, filed Oct. 6, 2020, the content of which is hereby incorporated by reference in its entirety.

FIELD

The field of this disclosure relates generally to apparatus for and methods of applying segments of material to a web, and more particularly to apparatus for and methods of shaping and applying segments of material to a moving web using side shifting pucks.

BACKGROUND

Absorbent garments, such as adult incontinence wear, infant and children's diapers, swim wear and training pants, include leg openings having an elastic portion around each leg opening, and a waist opening having an elastic portion at least partially surrounding the waist opening. The elastic portions about the leg openings are intended to fit snugly around a wearer's legs to inhibit leakage of body exudates from the absorbent garment. The leakage performance and aesthetic appearance of some absorbent garments can be improved by leg elastics having curvature and/or displacement (i.e., being profiled, nonlinear) along their lengths.

However, many known techniques for applying leg elastics to a moving web during the manufacture of absorbent garments are often limited in the amount of displacement (e.g., the amount of amplitude in a curved pattern) that can be achieved. Thus, leg elastics in most known absorbent garments produced at high line speeds are often straight or relatively straight. Known techniques for attempting to place leg elastics with any significant amount of displacement (i.e., curvature) onto a web at high line speeds have been unsatisfactory.

Thus, there exists a need for an apparatus and method suitable for shaping segments of material in highly shaped profiles, imparting a desired stretch profile to such segments, and applying such segments to a moving web (e.g., a web moving at high line speeds).

SUMMARY

In one aspect, an apparatus for conveying and applying a discrete part to a substrate includes a plurality of transfer puck assemblies, a drive assembly, and a translation mechanism. The plurality of transfer puck assemblies is adapted to convey the discrete part to the substrate, and each transfer puck assembly includes at least one puck segment. The drive assembly is configured to rotate each transfer puck assembly about a drive axis. The translation mechanism is configured to translate the at least one puck segment in an axial direction as the plurality of transfer puck assemblies are being rotated about the drive axis to move the discrete part to a profiled configuration prior to application of the profiled discrete part to the substrate.

In another aspect, an apparatus for conveying a discrete part and applying the discrete part to a substrate includes a plurality of transfer puck assemblies, a drive assembly, and a translation mechanism. The plurality of transfer puck assemblies is adapted to convey the plurality of discrete parts to the substrate, and each transfer puck assembly includes a first puck segment and a second puck segment. The drive assembly is configured to rotate each transfer puck assembly about a drive axis. The translation mechanism is configured to translate at least one of the first and second puck segments in an axial direction as the plurality of transfer puck assemblies are rotated about the drive axis to profile the discrete part prior to application of the profiled discrete part to the substrate.

In yet another aspect, a method of applying discrete parts to a substrate includes feeding a plurality of discrete parts towards a plurality of transfer puck assemblies rotatably coupled to a drive assembly. Each transfer puck assembly includes at least one puck segment. The method also includes receiving a discrete part of the plurality of discrete parts onto each of the transfer puck assemblies. The method further includes rotating each transfer puck assembly such that each transfer puck assembly conveys each discrete part to the substrate. The method also includes simultaneously translating the at least one puck segment in an axial direction to profile the discrete part of the plurality of discrete parts. The method further includes applying the discrete part of the plurality of discrete parts to the substrate such that the applied discrete part of the plurality of discrete parts has a profiled configuration.

BRIEF DESCRIPTION OF THE DRAWINGS

FIG. 24A is a schematic view of rib cams of the manufacturing process illustrated in FIG. 3.

FIG. 24B is another schematic view of the rib cams of the manufacturing process seen in FIG. 24A.

Corresponding reference characters indicate corresponding parts throughout the drawings.

DETAILED DESCRIPTION OF THE DRAWINGS

Figure 1:
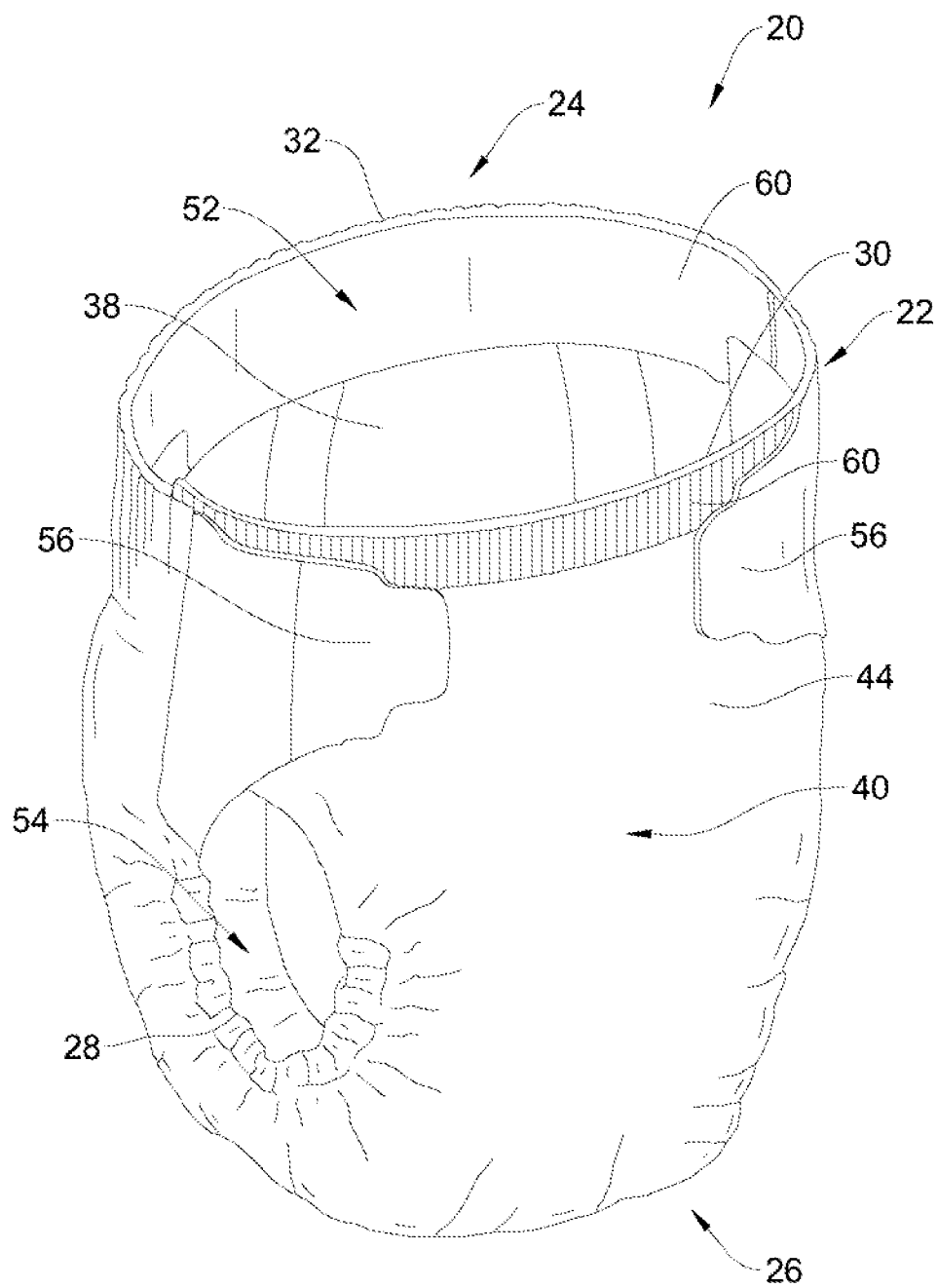
FIG. 1 is a front view of one suitable embodiment of an absorbent article with front and back waist regions of the article being joined together by a fastening assembly such that the article is in a pant-like configuration.
Figure 2:
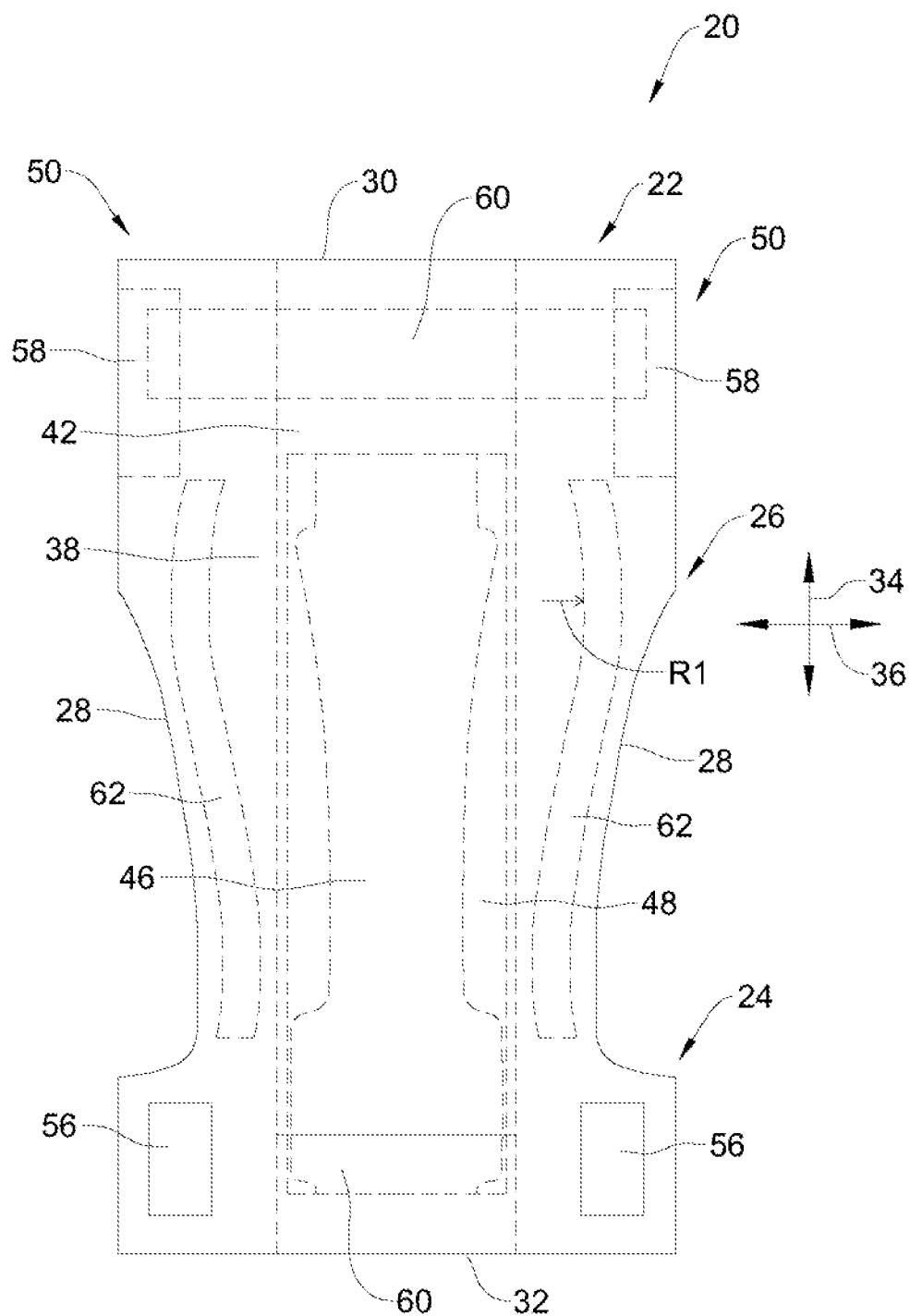
FIG. 2 is a plan view of the absorbent article of FIG. 1, the article being in a longitudinally stretched and laid-flat condition showing a surface of the article that faces the wearer during wear.

Referring now to the drawings and in particular to FIGS. 1 and 2, one suitable embodiment of an absorbent article or substrate is illustrated in the form of a child's diaper and is indicated generally by reference numeral 20. While the present disclosure will be made in the context of the diaper 20, it should be understood that aspects of the present disclosure are applicable to other absorbent articles, such as, for example, training pants, adult incontinence garments, diaper pants, swim diapers, feminine care articles and the like.

In one suitable embodiment, the diaper 20 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper 20 (or more broadly, the "absorbent article") can be reusable. That is, the absorbent article can be intended for multiple uses without departing from some aspects of this disclosure.

The diaper 20, as seen in FIGS. 1 and 2, has a front waist region 22, a back waist region 24, and a crotch region 26 disposed longitudinally between and interconnecting the front and back waist regions. The diaper 20 also has a pair of laterally opposite side edges 28 and a pair of longitudinally opposite waist edges, respectively designated front waist edge 30 and back waist edge 32. In the illustrated embodiment, the side edges 28 are arcuately shaped to provide the diaper 20 with a more body conforming shape. The front waist region 22 is contiguous with the front waist edge 30, and the back waist region 24 is contiguous with the back waist edge 32.

As seen in FIG. 2, the diaper 20 defines a longitudinal direction 34 and a transverse direction 36 perpendicular to the longitudinal direction. The diaper 20 includes a body-facing side 38 (i.e., the side of the diaper 20 that faces the body of a wearer when worn) and a garment-facing side 40 (i.e., the side of the diaper 20 that faces away from the body of a wearer when worn). The diaper 20 also includes a liquid impermeable backsheet 42, a topsheet 44, and an absorbent assembly, indicated generally at 46, disposed between the backsheet and the topsheet. The illustrated absorbent assembly 46 extends longitudinally from the front waist region 22 through the crotch region 26 to the back waist region 24. As seen in FIG. 2, the backsheet. 42, topsheet. 44, and absorbent assembly 46 are arranged in a superposed relation by suitable means including, but not limited to, adhesives, ultrasonic bonds, pressure bonds, thermal bonds, and combinations thereof. The absorbent assembly 46 also includes a pair of containment flaps 48 for inhibiting the lateral flow of body exudates.

Suitably, the backsheet 42 prevents waste material from wetting articles, such as bed sheets and clothing, as well as the wearer and caregiver. The backsheet may comprise a variety of suitable materials including, for example and without limitation, a material which is substantially liquid impermeable. The backsheet 42 can be a single layer of liquid impermeable material, or may comprise a multi-layered laminate structure in which at least one of the layers is liquid impermeable. The backsheet 42 may also comprise a liquid permeable material.

The backsheet 42 may also be stretchable, and more suitably elastic. In particular, the backsheet 42 is suitably stretchable and more suitably elastic in at least the transverse, or circumferential direction 36 of the diaper 20. The backsheet 42 may also be stretchable, and more suitably elastic, in both the transverse and the longitudinal directions 34 and 36.

The topsheet 44 is suitably compliant, soft-feeling, and non-irritating to the wearer's skin. The topsheet 44 is also sufficiently liquid permeable to permit liquid body exudates to readily penetrate through its thickness to the absorbent assembly 46. The topsheet 44 may comprise a variety of suitable materials including, for example and without limitation, porous foams, reticulated foams, apertured plastic films, woven and nonwoven webs, and combinations thereof. The topsheet 44 may also be stretchable, and more suitably it may be elastomeric.

The absorbent assembly 46 is suitably compressible, conformable, non-irritating to a wearer's skin, and capable of absorbing and retaining liquids and certain body wastes. For example, the absorbent assembly 46 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The absorbent assembly 46 may be stretchable so as not to inhibit the stretchability of other components to which the absorbent structure may be adhered, such as the backsheet 42 and topsheet 44. After being formed or cut to a desired shape, the absorbent assembly 46 may be wrapped or encompassed by a suitable wrap (not shown) that aids in maintaining the integrity and shape of the absorbent structure.

The absorbent assembly 46 may also include a surge management layer (not shown) located adjacent the absorbent assembly 46 (e.g., between the absorbent assembly 46 and the topsheet 44) to decelerate and diffuse surges or gushes of liquid that may be rapidly introduced into the absorbent assembly 46 of the diaper 20 by the wearer. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the disclosures of which are hereby incorporated by reference.

As seen in FIG. 1, the front waist region 22 of the diaper 20 can be selectively joined to the back waist region 24 via a pair of refastenable side seams 50 to define a fastened or wear configuration of the diaper having a waist opening, indicated at 52, and two leg openings, indicated at 54. The illustrated refastening seams 50 are defined by first fastening components 56 (e.g., a loop-type fastener) selectively engageable with second fastening components 58 (e.g., hook-type fasteners). The fastening components 56, 58 may include any suitable complementary refastenable fasteners including, for example and without limitation, hook- and loop-type fasteners, other types of mechanical fasteners, adhesive fasteners, cohesive fasteners, and combinations thereof. In some suitable embodiments, the fastening components 56, 58 may be pre-fastened during the manufacturing process of the diaper 20 such that the diaper 20 is supplied to the user in the fastened configuration. While FIG. 1 illustrates the front and back regions 22, 24 being joined together via refastenable seams 50, it is understood that the front and back regions can be joined together via non-refastenable, bonded seams (e.g., by adhesive bonding, ultrasonic bonding, pressure bonding, thermal bonding).

With reference still to FIGS. 1 and 2, the illustrated diaper 20 also includes front and rear waist elastic members 60 configured to form a gasket around the waist opening 52. The waist elastic members 60 can be formed of any suitable elastic material including, for example and without limitation, sheets, strands or ribbons of natural rubber, synthetic rubber, or thermoplastic elastomeric polymers. Other suitable elastic materials from which the waist elastic members 60 can be formed, and suitable methods of incorporating waist elastic members into an absorbent article are described in U.S. Pat. No. 9,820,889 filed Oct. 31, 2013 by Sina et al., and U.S. Pat. No. 9,265,669 filed Oct. 31, 2013 by Bennett et al., the disclosures of which are hereby incorporated by reference.

As best seen in FIG. 2, the illustrated diaper 20 also includes a pair of profiled leg cuffs or discrete parts 62 disposed proximate the side edges 28 of the diaper 20 to create a gasket and to reduce or inhibit leakage of body exudates around the leg openings 54. The leg cuffs 62 can be formed from a variety of suitable elastic materials including, for example and without limitation, sheets, strands or ribbons of natural rubber, synthetic rubber, or thermoplastic elastomeric polymers. The illustrated leg cuffs 62 include at least one elastic element (e.g., an elastic strand) adhered to the topsheet 44. Suitably, the leg cuffs 62 can be cut and formed from a continuous ribbon of elastic material, and applied to the diaper 20 as a discrete segment utilizing the apparatus and methods described in more detail herein.

Particular examples of suitable elastic materials for leg cuffs 62 include, without limitation, dry-spun coalesced multifilament spandex elastomeric threads sold under the trade name LYCRA® and available from Invista of Wichita, Kansas, U.S.A., vertical filament laminate (VFL) materials, an example of which is described in U.S. Pat. No. 6,916,750 to Thomas et al., which is hereby incorporated by reference; elastic nonwoven composites having an apertured elastic film laminated to one or more nonwoven web materials, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are hereby incorporated by reference; and other elastic laminates such as single- and dual-faced spandex laminates, stretch-bonded laminates (SBL), and continuous filament stretch-bonded laminates (CFSBL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are hereby incorporated by reference.

In the illustrated embodiment, the leg cuffs 62 are attached to the body-facing side 38 of the topsheet 44. In other suitable embodiments, the leg cuffs 62 may be attached to the garment-facing side 40 of topsheet 44. In yet other suitable embodiments, it is contemplated that the leg cuffs 62 can be attached to the body-facing side 38 of the backsheet 42 in addition to, or instead of, the leg cuffs 62 being attached to the topsheet 44. That is, in one suitable embodiment, the leg cuffs 62 can be attached to both the body-facing and garment-facing sides 38, 40 of the topsheet 44.

As shown in FIG. 2, the leg cuffs 62 of the illustrated embodiment are profiled and, more specifically curved (i.e., nonlinear), to provide a more formfitting, comfortable gasket around the leg openings 54 of the diaper 20. In particular, the leg cuffs 62 are shaped to provide improved leakage protection and a more appealing aesthetic appearance. More specifically, at least a portion of each leg cuff 62 has a radius of curvature R of less than about 40 inches, and more suitably less than about 10 inches, along at least a portion of its length.

Figure 3:
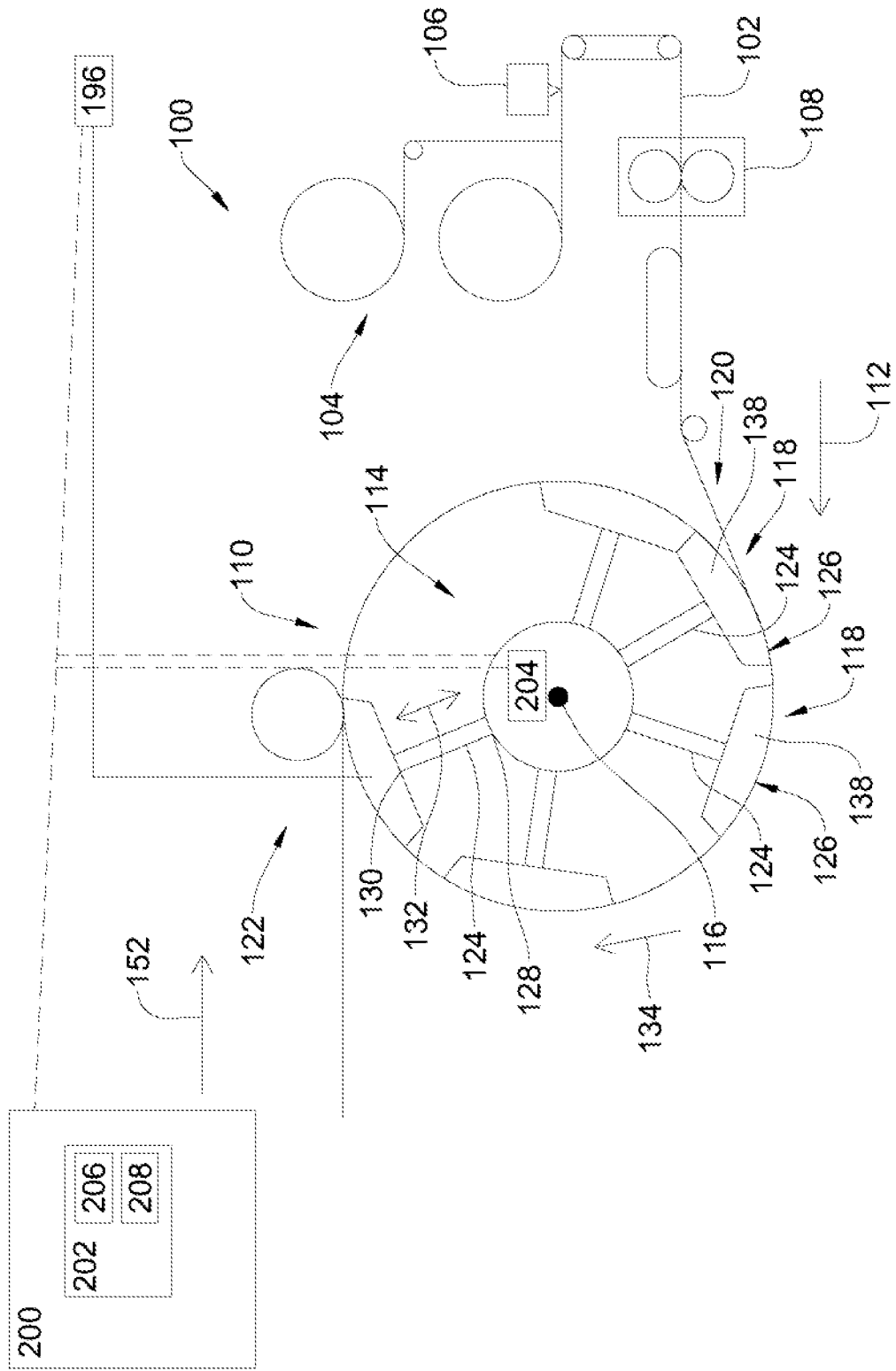
FIG. 3 illustrates one suitable embodiment of a manufacturing process for manufacturing the absorbent article illustrated in FIGS. 1 and 2.
Figure 4:
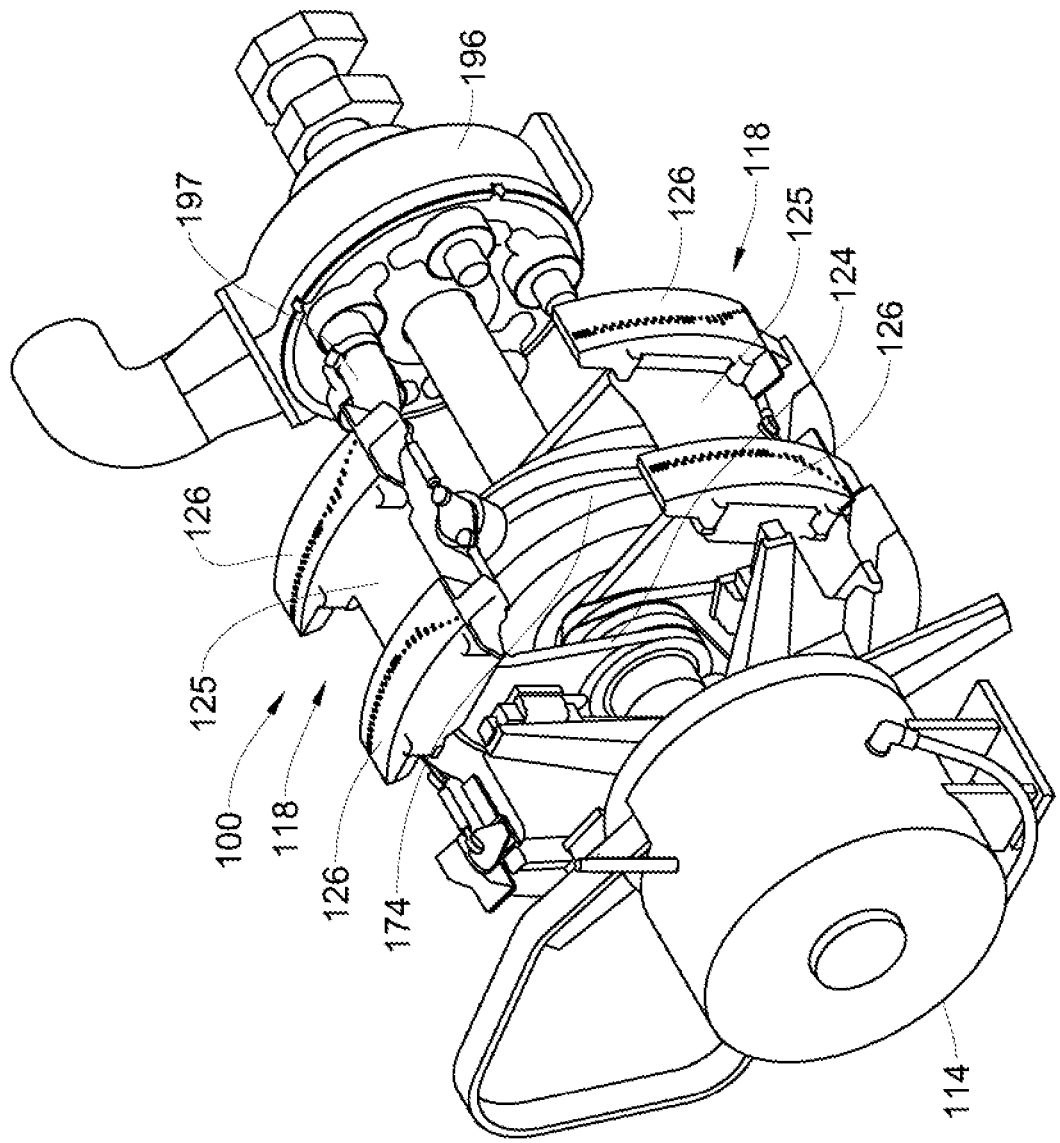
FIG. 4 illustrates a perspective view of the manufacturing process illustrated in FIG. 3.
Figure 5:
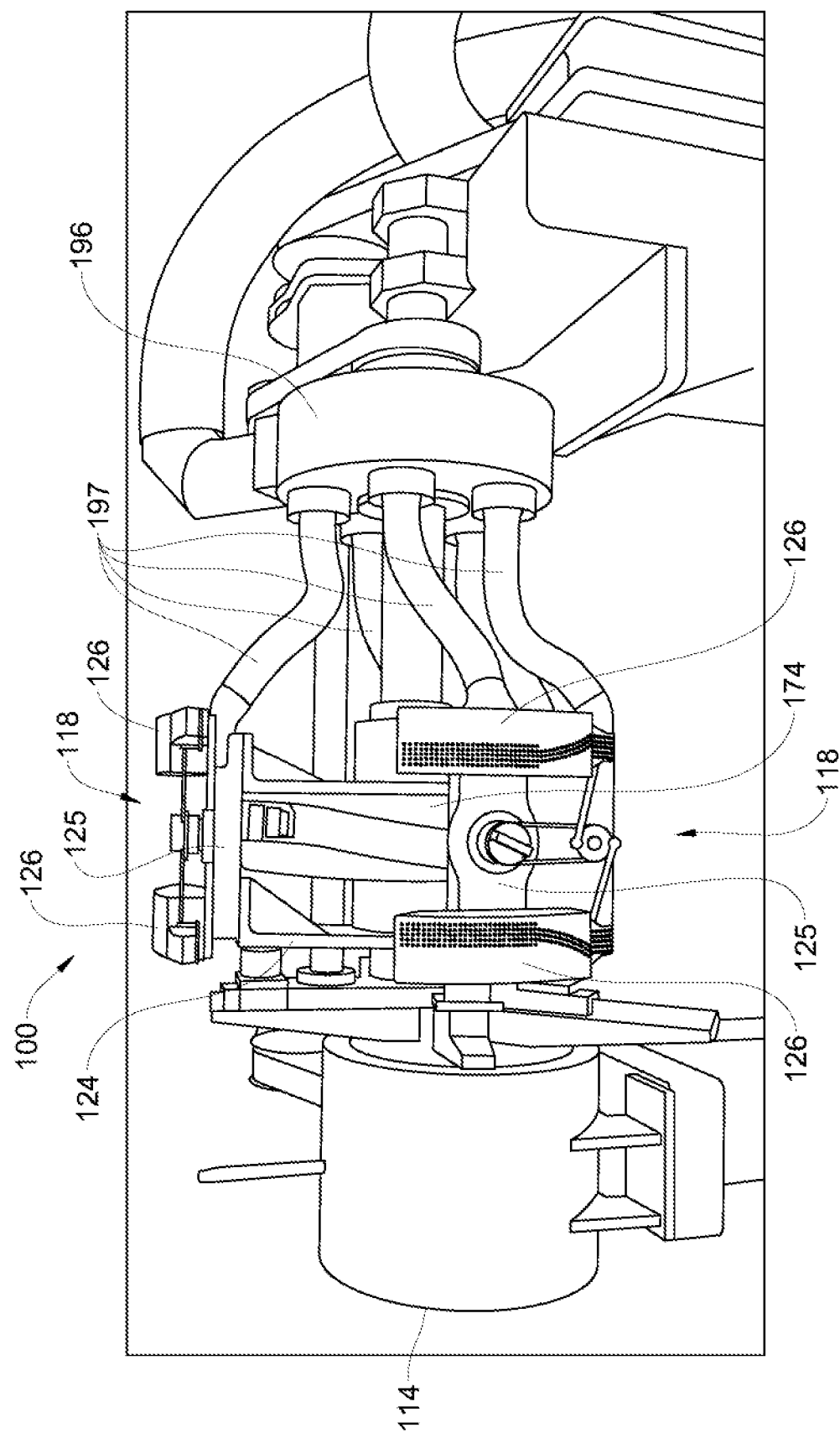
FIG. 5 illustrates a side perspective view of the manufacturing process illustrated in FIG. 3.

FIG. 3 schematically illustrates a portion of one suitable embodiment of a process 100 for making the absorbent articles 20 illustrated in FIGS. 1 and 2. FIG. 4 is a perspective view of the process 100 for making the absorbent articles 20 illustrated in FIGS. 1 and 2. FIG. 5 is a perspective side view of the process 100 for making the absorbent articles 20 illustrated in FIGS. 1 and 2. As seen in FIG. 3, at least one supply of a web 102 is used to form the leg cuffs 62 of the absorbent article 20 and is provided from suitable supply sources (e.g., supply rolls 104). As shown in FIG. 3, the process 100 includes two supplies of web 102 and two supply rolls 104 to simultaneously apply the leg cuffs 62 to the absorbent article 20. However, the process 100 may include only a single supply of the web 102 and a single supply roll 104.

The process 100 includes at least one applicator 106, a perforator 108, and a web treatment apparatus 110. The applicator 106 applies a hot melt adhesive (not shown) to the web 102, and the hot melt adhesive adheres the leg cuffs 62 to the absorbent articles 20. The applicator 106 may include, but is not limited to only including, a spray, a slot coat, a drag bead, and/or any other suitable type of adhesive applicator.

The web 102 is fed to the web treatment apparatus 110 to assemble at least a portion of the absorbent article 20. Specifically, the treatment apparatus 110 receives the web 102 as it is traveling in a first direction, represented by arrow 112. In this embodiment, the web 102 includes two continuous ribbons of elastic material 106. In another suitable embodiment including only a single supply of the web 102 and a single supply roll 104, the web 102 includes a continuous ribbon of elastic material 106 that is separated into separated, discrete leg cuffs 62. In the illustrated embodiment, the perforator 108 at least partially perforates the continuous ribbon of elastic material 106. More specifically, in this embodiment, the perforator 108 partially perforates the continuous ribbon of elastic material 106 such that the continuous ribbon of elastic material 106 is weakened, but does not separate into separate leg cuffs 62. Rather, and as described below in more detail, the treatment apparatus 110 separates the continuous ribbon of elastic material 106 into separate leg cuffs 62. In another suitable embodiment, the web 102 includes leg cuffs 62 that are separated by preformed perforations or other suitable lines of weakness. It is contemplated, however, that pre-separated leg cuffs 62 can be fed to the treatment apparatus 110. It is also contemplated that the web 102 can be cut into separate leg cuffs 62 after the web 102 is fed to the treatment apparatus 110.

In one embodiment, the treatment apparatus 110 includes a drive assembly 114 configured to rotate about a drive axis 116, and a plurality of transfer segments 118 that are coupled to and extend outwardly from the drive assembly. The drive assembly 114 includes one or more drive sources including, for example, servo motors, and/or camboxes, that are coupled to each transfer segment 118. The drive assembly 114 is configured to rotate each transfer segment 118 about the drive axis 116 between a pick-up location, indicated generally at 120, and an application location, indicated generally at 122.

As illustrated in FIG. 3, the transfer segment 118 is configured to receive the web 102 including the leg cuffs 62 at the pick-up location 120, and convey the leg cuffs 62 to the application location 122. In the illustrated configuration, each of the leg cuffs 62 is separated from an adjacent leg cuff 62 along the perforation (or other line of weakness) formed by the perforator 108 as the web 102 is conveyed by the treatment apparatus 110. More specifically, and as described below in more detail, each of the leg cuffs 62 is received by one of the transfer segments 118. During rotation by the drive assembly 114, each of the adjacent transfer segments 118 of the treatment apparatus 110 moves apart thereby causing the web 102 of leg cuffs 62 to rupture (i.e., separate) about the perforations. Thus, each of the transfer segments 118 is adapted to carry the leg cuffs 62 of one of the absorbent articles 20.

In a suitable embodiment, the web treatment apparatus 110 is an oscillating cam adjusted roller as is disclosed in U.S. Pat. Nos. 5,716,478, 5,759,340, and 6,139,004, all of which are assigned to Kimberly-Clark Worldwide, Inc., and the entire disclosures of all of which are hereby incorporated herein by reference.

Each of the transfer segments 118 includes a support arm 124 extending radially outwardly from the drive assembly 114, and a transfer puck assembly 126 coupled to the support arm 124. The transfer puck assembly 126 includes a puck support 125 and at least one puck assembly 127 attached to the puck support. In this embodiment, the transfer puck assembly 126 includes two puck assemblies 127. The support arm 124 includes a first end 128, which is coupled to the drive assembly 114, and an opposite second end 130, which is coupled to the puck support 125 of the transfer puck assembly 126. The support arm 124 extends between the first end 128 and the second end 130 along a radial axis 132. In one suitable embodiment, the first end 128 of the support arm 124 is coupled to the drive assembly 114 such that each transfer puck assembly 126 is independently rotatable about the drive axis 116 of the treatment apparatus 110 (as indicated by arrow 134 of FIGS. 3 and 10) and at least one puck segment 138 of a plurality of puck segments 138 of each puck assembly 127 is translatable along an axial direction (as indicated by arrow 136 of FIG. 6A).

Figure 6:
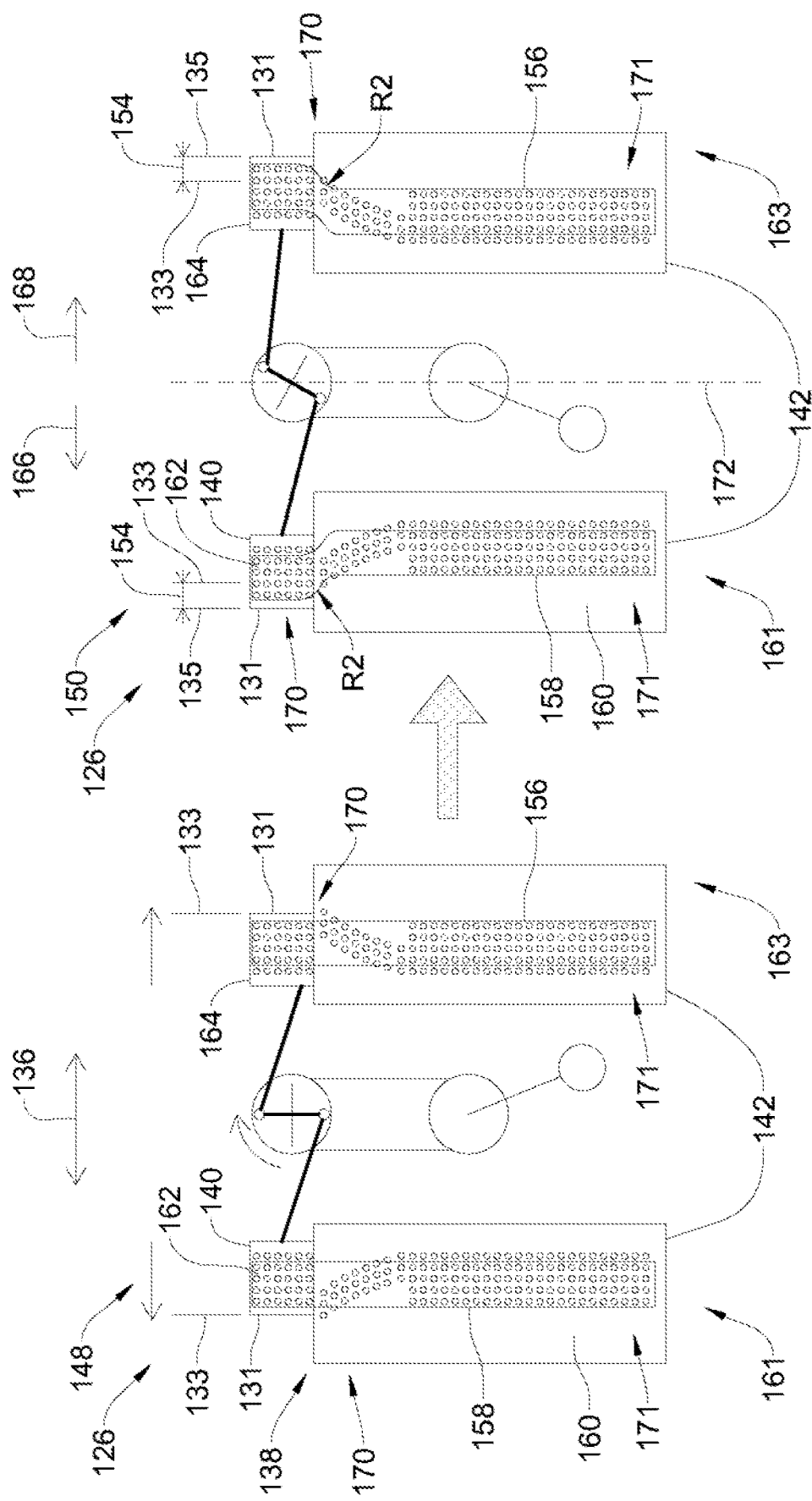
FIG. 6A is a top view of a transfer puck assembly of the manufacturing process illustrated in FIGS. 3-5 in a first position.
FIG. 6B is a top view of the transfer puck assembly seen in FIG. 6A moved to a second position.
Figure 7:
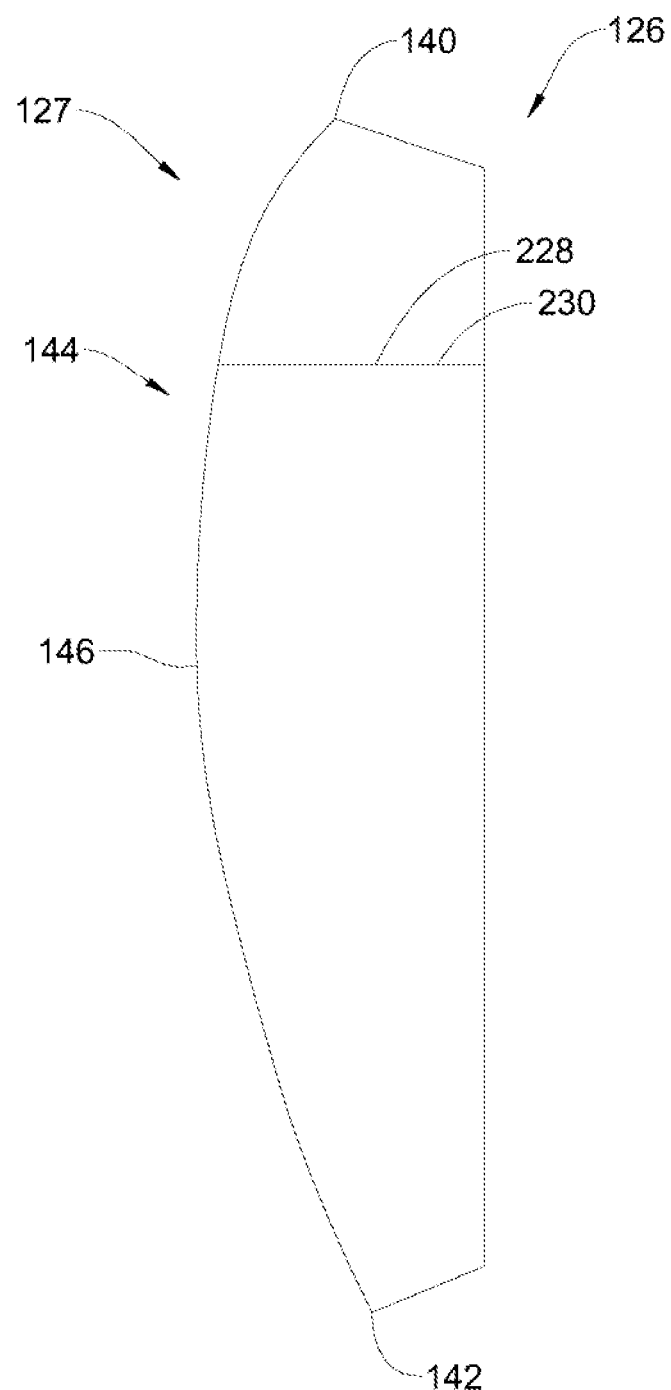
FIG. 7 is a side view of the transfer puck assembly illustrated in FIGS. 6A and 6B.

As illustrated in FIGS. 6A, 6B, and 7, each puck assembly 127 includes the plurality of puck segments 138 that define a leading edge 140, a trailing edge 142, and a platform 144 of the transfer puck assembly 126. The platform 144 extends between the leading edge 140 and the trailing edge 142 and is sized and shaped to receive the leg cuffs 62 from the web 102, and release the leg cuffs 62 to apply the leg cuffs 62 to the absorbent article 20. Specifically, as shown in FIG. 7, the platform 144 has a curved shape that matches a curved outer contour 146 of the apparatus 110.

As mentioned above, the puck segments 138 of the puck assembly 127 are translatable in the axial direction 136 to curve a curved end 170 of the leg cuffs 62 prior to applying the leg cuffs 62 to the absorbent article 20. More specifically, at least one puck segment 138 of each puck assembly 127 is movable between a first position, indicated generally at 148 in FIG. 6A, wherein the puck assembly is oriented to receive the leg cuffs 62 at the pick-up location 120 and a second position, indicated generally at 150 in FIG. 6B, wherein the puck assembly 127 is oriented to apply the leg cuffs 62 to the absorbent article 20 at the application location 122.

In one suitable embodiment, the web 102 of leg cuffs 62 is traveling at a first speed in the first direction 112, and the absorbent article 20 is traveling at a second speed in a second direction 152 that is different than the first speed. The drive assembly 114 is adapted to rotate each transfer puck assembly 126 about the drive axis 116 such that the surface speed of each puck assembly 127 is approximately equal to the speed of the web 102 as the leg cuffs 62 are received by the platforms 144 of the puck assembly 127 at the pick-up location 120. In the illustrated embodiment, the drive assembly 114 accelerates each transfer puck assembly 126 such that the speed of the puck assembly 127 is approximately equal to the speed of the absorbent article 20 as the leg cuffs 62 are applied to the absorbent article 20 by the puck assembly 127 at the application location 122. Additionally, accelerating the transfer puck assemblies 126 separates the puck assemblies 127 such that the web 102 is separated into the leg cuffs 62 along the perforations (or other line of weakness) prior to applying the leg cuffs 62 to the absorbent articles 20.

In one embodiment, at least one puck segment 138 of each of the puck assemblies 127 is translated along axial direction 136. A cylinder or barrel cam 174 causes at least one puck segment 138 of each puck assembly 127 to translate along axial direction 136 between the pick-up location 120 and the application location 122. In one suitable embodiment, the barrel cam 174 is configured to selectively adjust a translation distance of at least one puck segment 138 of each puck assembly 127, as at least one puck segment 138 of each puck assembly 127 is translated between the pick-up location 120 and the application location 122. More specifically, the barrel cam 174 selectively translates at least one puck segment 138 of each puck assembly 127 from the first position 148 to the second position 150 from the pick-up location 120 to the application location 122 such that an outer edge 131 of each puck segment 138 is translated from a first location 133 to a second location 135. The distance between the first location 133 of the first position 148 and the second location 135 of the second position 150 defines a translation distance 154 traveled by the puck segment 138.

In one suitable embodiment, the apparatus 110 can be used to simultaneously apply first and second leg cuffs 156, 158 to a continuously moving product web including at least one portion of the absorbent article 20. In the illustrated embodiment, the translation distance 154 of the first and second leg cuffs 156, 158 is the same. In alternative embodiments, the translation distance 154 of the first and second leg cuffs 156, 158 is different.

FIG. 6A is a top view of the transfer puck assembly 126 of the manufacturing process 100 in the first position 148, and FIG. 6B is a top view of the transfer puck assembly seen in FIG. 6A moved to the second position 150. In the illustrated embodiment, the transfer puck assembly 126 includes a first puck assembly 161 and a second puck assembly 163. The first and second puck assemblies 161 and 163 each include a base puck segment 160 and a translating puck segment 162, 164. Specifically, the first puck assembly 161 includes a first translating puck segment 162, and the second puck assembly 163 includes a second translating puck segment 164. The barrel cam 174 is configured to translate the first translating puck segment 162 along axial direction 136 in a first translation direction, represented by arrow 166 in FIG. 6B, and to translate the second translating puck segment 164 in a second translation direction, represented by arrow 168 in FIG. 6B, that is opposite the first direction. The translating puck segments 162, 164 may be disposed on or connected to linear bearings or the like to ensure accurate linear movement. Translating the first and second translating puck segments 162, 164 curves the curved end 170 of the first and second leg cuffs 156, 158 prior to adhering the first and second leg cuffs 156, 158 to the absorbent article 20. Additionally, a straight end 171 of the first and second leg cuffs 156, 158 is maintained in position as the curved end 170 is translated along the axial direction 136. That is, only a portion of the first and second leg cuffs 156, 158 is translated along the axial direction 136, while another portion of the first and second leg cuffs is maintained in position.

The first puck assembly 161 conveys the first leg cuff 156, and the second puck assembly 163 conveys the second leg cuff 158. The first translating puck segment 162 is translated in the first translation direction 166, and the second translating puck segment 164 is translated in the second translation direction 168 such that the curved end 170 of the first leg cuff 156 is spaced from the curved end 170 of the second leg cuff 158.

In the embodiment illustrated in FIGS. 6A and 6B, each of the first and second translating puck segments 162, 164 is translated such that the curved end 170 of the first and second leg cuffs 156, 158 are applied to the absorbent article 20 with the radius of curvature R. In another embodiment, each of the first and second translating puck segments 162, 164 is translated to different translation distances 154 such that the curved end 170 of the first and second leg cuffs 156, 158 are applied at different radius of curvatures R. More specifically, each of the first and second translating puck segments 162, 164 is translated to different translation distances 154 such that the curved end 170 of the first leg cuff 156 is applied at a first radius of curvature R1 and the curved end 170 of the second leg cuff 158 is applied at a second radius of curvature R2 that is different than the first radius of curvature R1. In one suitable embodiment, the second leg cuff 158 is applied at the second radius of curvature R2 that is equal to, and opposite from, the first radius of curvature R1. By applying the first and second leg cuffs 156, 158 at opposing, curved orientations, the apparatus 110 can manufacture the absorbent article 20 of FIGS. 1 and 2.

Figure 8:
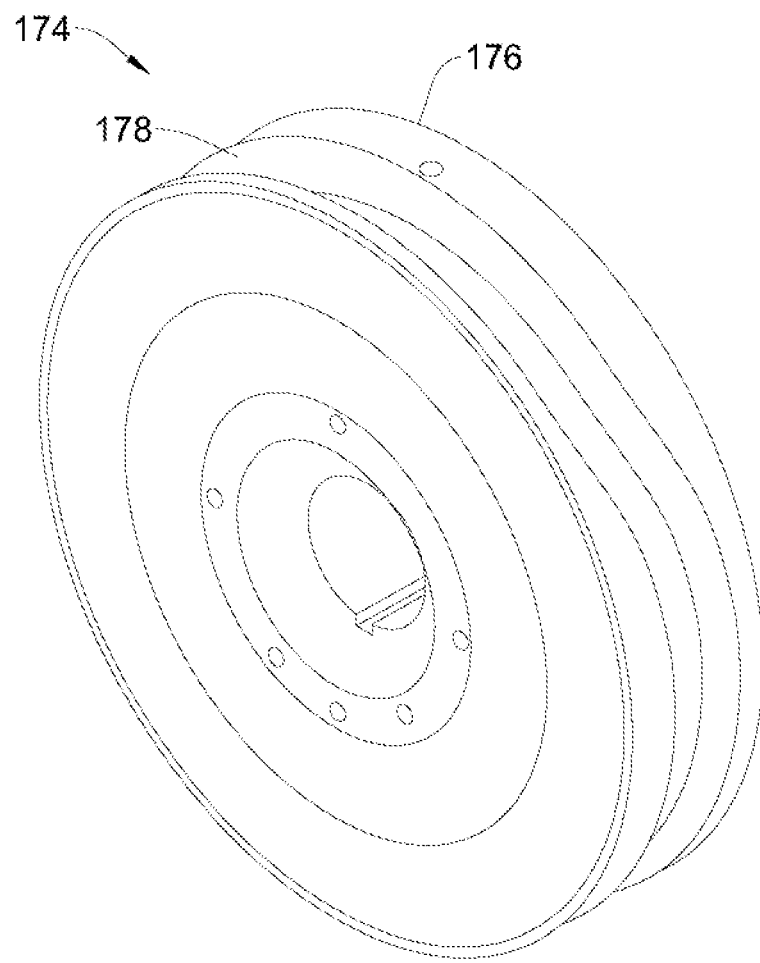
FIG. 8 is a perspective view of a barrel cam of a translation mechanism of the manufacturing process illustrated in FIGS. 3-5.
Figure 11:
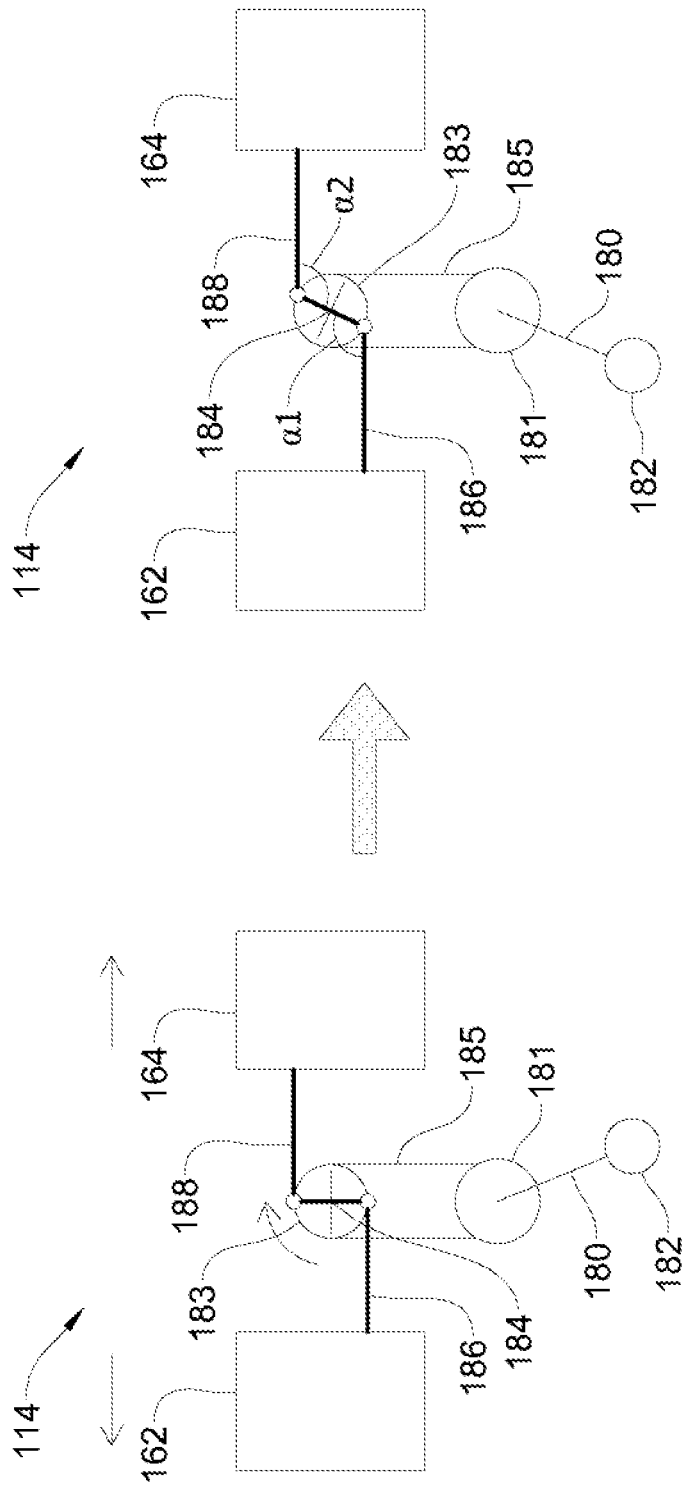
FIG. 11A is a schematic view of a portion of a follower and a linkage assembly of the barrel cam illustrated in FIG. 5.
FIG. 11B is a schematic view of the portion of the follower and the linkage assembly of the barrel cam seen in FIG. 11A moved to a second position.

In one suitable embodiment illustrated in FIG. 8, the cylinder or barrel cam 174 is coupled to each puck assembly 127 to translate the respective puck segments 138 of each transfer puck assembly 126 along the axial direction 136. The barrel cam 174 includes a radial outer surface 176 and a cam track 178 defined along the radial outer surface. As illustrated in FIGS. 11A and 11B, each transfer puck assembly 126 includes a cam arm 180, a cam follower 182 coupled to the cam arm 180, a first cam pivot 181 also coupled to the cam arm 180, a second cam pivot 183, and a cam belt 185 coupled to both of the first and second cam pivots. The cam follower 182 is positioned within the cam track 178 and moves from a first position 187 illustrated in FIG. 11A to a second position 189 illustrated in FIG. 11B. Specifically, the cam track 178 has a curved shape, and the cam follower 182 follows the curved shape of the cam track. The cam arm 180 is attached to the cam follower 182 and rotates as the cam follower moves between the first position 187 and the second position 189. The cam arm 180 is also attached to the first cam pivot 181 and rotates the first cam pivot. The first cam pivot 181 rotates the cam belt 185 which rotates the second cam pivot 183.

The second cam pivot 183 is coupled to the first and second translating puck segments 162, 164, and includes a pivot point 184. In one embodiment, the apparatus 110 includes a first translation segment 186 associated with the first translating puck segment 162 and a second translation segment 188 associated with the second translating puck segment 164. The second cam pivot 183 is coupled to the first and second translation segments 186 and 188 such that rotation of the second cam pivot translates the first and second translating puck segments 162, 164 along the axial direction 136. The cam follower 182 is adapted to engage the cam track 178 to facilitate selectively translating the first and second translating puck segments 162, 164 along the axial direction 136. More specifically, the cam follower 182 rotates the cam arm 180, the cam arm rotates the first cam pivot 181, the first cam pivot rotates the cam belt 185, the cam belt rotates the second cam pivot 183 about the pivot point 184, and the second cam pivot translates the first and second translation segments 186 and 188 and the first and second translating puck segments 162, 164 as each transfer puck assembly 126 rotates about the drive axis 116. Through connection with the translation segments 186, 188, the rotation of the cam arm 180 causes translation of the first and second translation segments 186 and 188 and the first and second translating puck segments 162, 164 along the axial direction 136.

It should be understood that many other options exist for converting the rotational motion of the cam arm 180 into the translation motion of the puck segments 162, 164. Accordingly, the specific mechanism shown in FIGS. 11A, 11B should not be viewed as limiting. For example, the process 100 may include other mechanisms for translating puck segments 162 and 164 such as: (1) two linear servos (not shown), one attached to each puck segment, that each translate at least one of first and second puck segments along axial direction 136; (2) a single linear servo 260 (shown in FIGS. 23A and 23B) that actuates a rack and pinion system 262 (shown in FIGS. 23A and 23B) that translates first and second puck segments along axial direction 136; (3) two rib cams 270 (shown in FIGS. 24A and 24B), one attached to each puck segment, that each translate first and second puck segments along axial direction 136; and/or (4) any other mechanism that translates first and second puck segments along axial direction 136 as described herein.

Figure 23A:
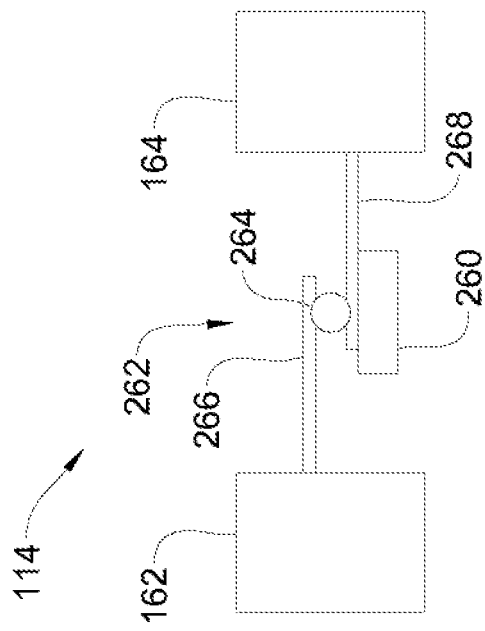
FIG. 23A is a schematic view of a linear servo and a rack and pinion system of the manufacturing process illustrated in FIG. 3.
Figure 23B:
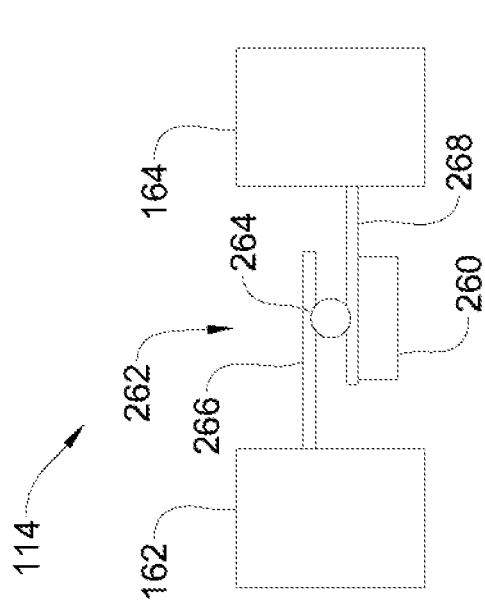
FIG. 23B is another schematic view of the linear servo and the rack and pinion system of the manufacturing process seen in FIG. 23A.

Specifically, in the alternative embodiment illustrated in FIGS. 23A and 23B, each transfer puck assembly 126 may include the linear servo 260 and the rack and pinion system 262 attached to the linear servo for translating first and second puck segments along axial direction 136. The rack and pinion system 262 includes a pinion 264, a first rack 266 attached to the first puck segment 162 and movably attached to the pinion, and a second rack 268 attached to the second puck segment 164 and movably attached to the pinion. The first rack 266 is also slidably attached to the linear servo 260. Rotation of the transfer segment 118 actuates the linear servo 260, and the linear servo translates the first rack 266 and the first puck segment 162 along axial direction 136 as described herein. Translation of the first rack 266 also rotates the pinion 264. Rotation of the pinion 264 translates the second rack 268 and the second puck segment 164 along axial direction 136 as described herein.

Additionally, in the alternative embodiment illustrated in FIGS. 24A and 24B, each transfer puck assembly 126 may include the two rib cams 270, one attached to each puck segment 162 and 164, that each translate first and second puck segments along axial direction 136. Each rib cam 270 includes a rib 272 extending from the radial outer surface 176 of the barrel cam 174, a cam follower 274 movably attached to the rib 272, and a cam arm 276 attached to the cam follower 274 and the first and second puck segments 162 and 164. The cam followers 274 are positioned on the ribs 272, and the ribs 272 have a curved shape similar to the cam track 178. The cam followers 274 follow the curved shape of the ribs 272, and the cam arms 180 translate the first and second puck segments 162 and 164 as the cam followers and the cam arms follow the curved shape of the ribs.

Figure 9:
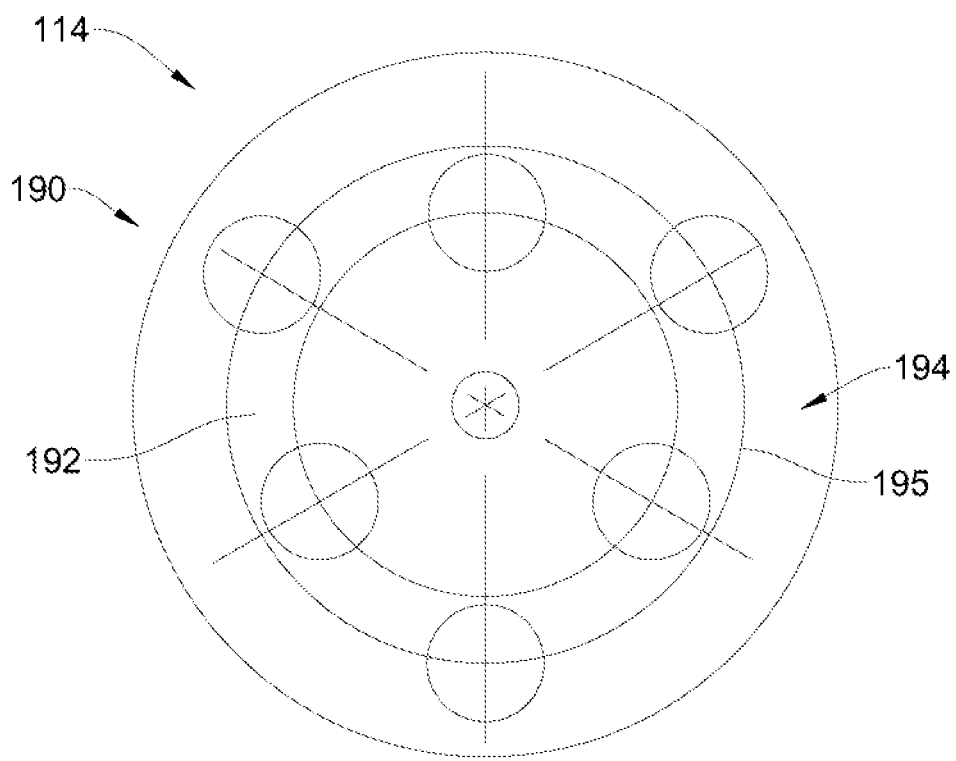
FIG. 9 is a side sectional view of a drive ring assembly and a cam plate assembly of the manufacturing process illustrated in FIGS. 3-5.
Figure 10:
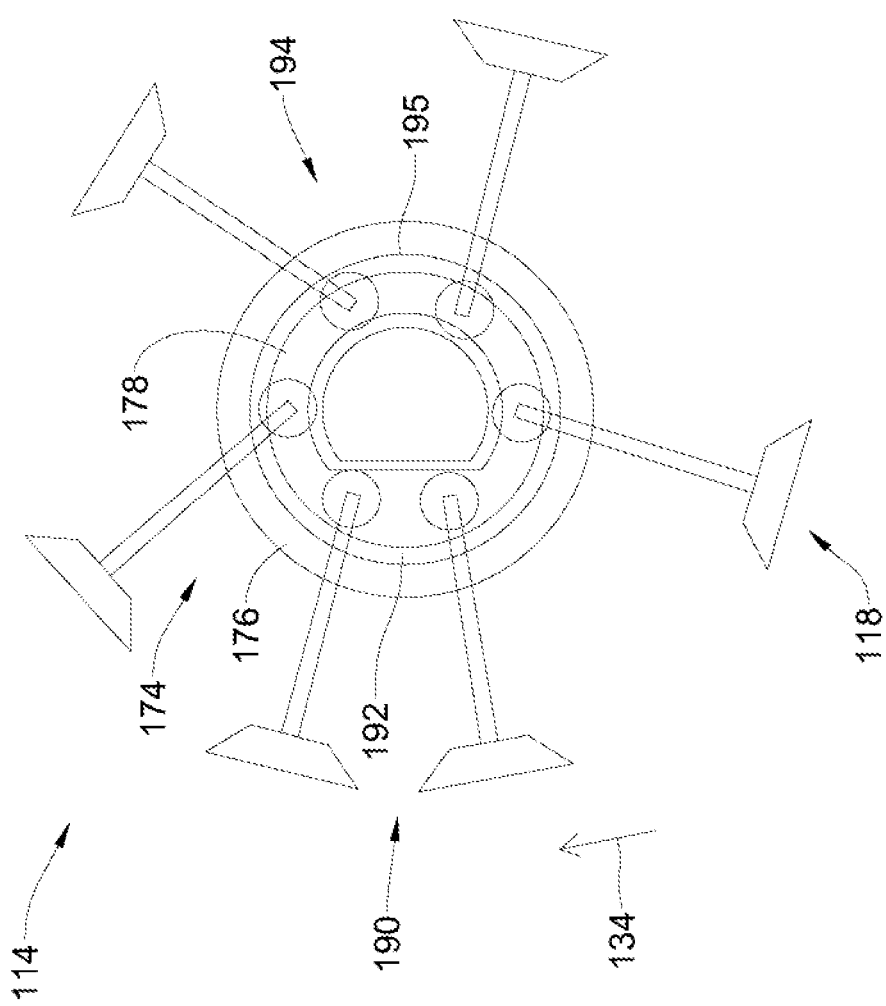
FIG. 10 is a side sectional view of the drive ring assembly, the cam plate assembly, and the transfer segments of the manufacturing process illustrated in FIGS. 3-5.

FIGS. 9 and 10 are schematic views of a portion of one suitable embodiment of the drive assembly 114. As mentioned above, the apparatus 110 includes a plurality of transfer puck assemblies 126 each comprising at least the first translating puck segment 162 and the second translating puck segment 164. The illustrated drive assembly 114 is configured to rotate each transfer puck assemblies 126 about the drive axis 116 and translate the first and second translating puck segments 162, 164 such that the curved ends 170 of the first and second leg cuffs 156, 158 are curved away from each other.

As seen in FIGS. 9 and 10, the drive assembly 114 includes a drive ring assembly 190 and a cam plate assembly 192. The drive ring assembly 190 and cam plate assembly 194 are each coupled to each transfer segment 118 to rotate the transfer segments about the drive axis 116. The drive ring assembly 190 includes a drive ring 194. In another embodiment, the drive ring assembly 190 includes a plurality of drive rings (not shown). As illustrated in FIG. 9, the cam plate assembly 194 includes a cam plate 195 including the cam track 178.

In one embodiment, the drive ring 194 and the cam track 178 are coupled to each transfer segment 118. The drive ring 194 rotates each transfer segment 118 about drive axis 116, and the cam track 178 engages cam follower 182 to translate the puck segments 138 along axial direction 136 as the transfer segments 118 are rotated about drive axis 116.

Figure 12:
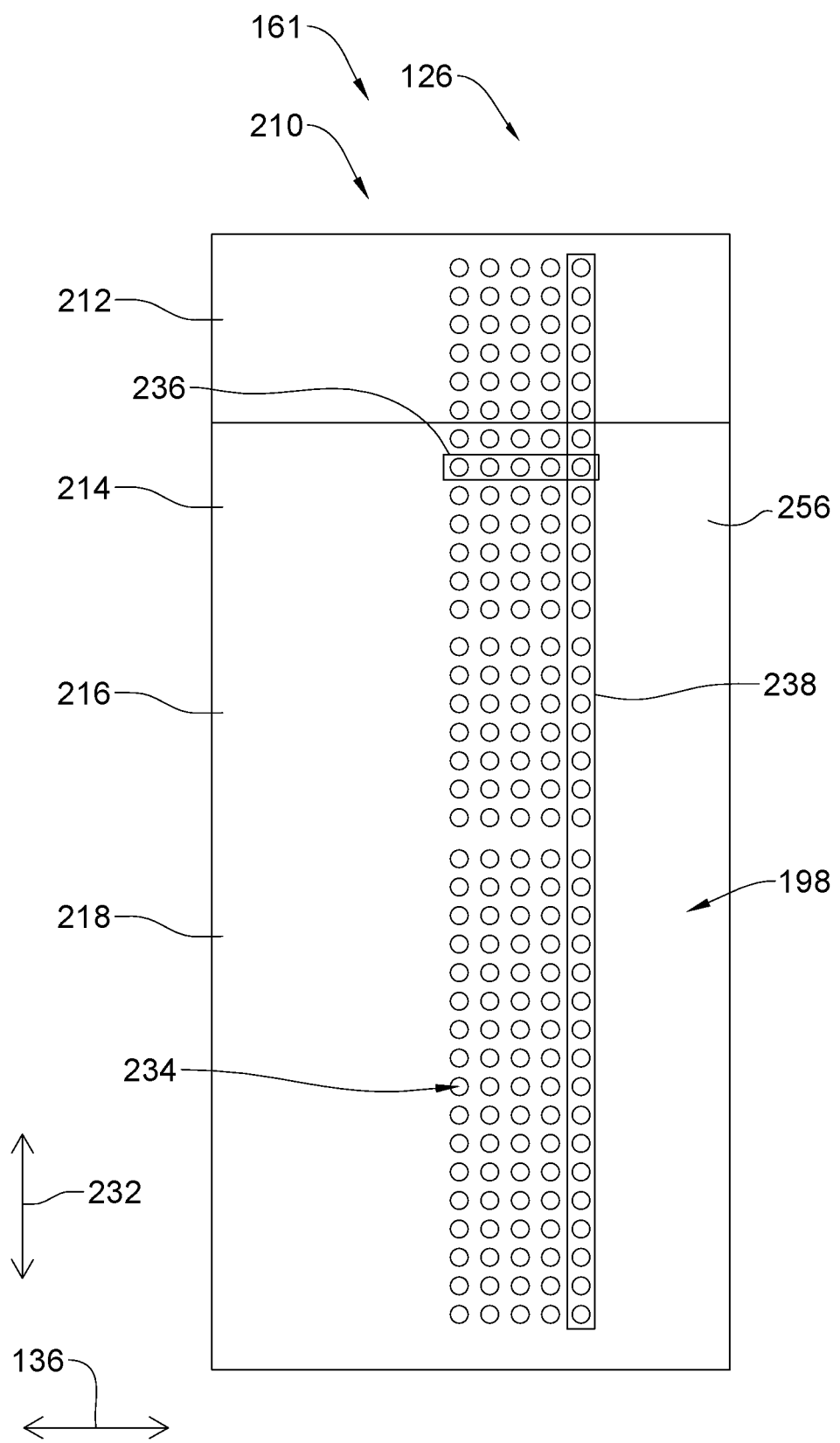
FIG. 12 is a schematic view of the transfer puck assembly illustrated in FIGS. 3-5 arranged in a first transfer puck assembly arrangement.

Referring to again to FIGS. 3-5, in a suitable embodiment, the apparatus 110 includes a vacuum assembly 196 that is coupled to each puck support 125 by a vacuum hose 197 to selectively apply a vacuum suction to the platform 144 through the puck support 125 to enable the transfer puck assembly 126 to selectively receive, hold and release the respective leg cuffs 62. More specifically, as shown in FIG. 12, the puck segments 138 define a plurality of vacuum holes 198 that are fluidly connected to the vacuum assembly 196. The vacuum assembly 196 selectively applies a vacuum suction through the vacuum hose 197, the puck support 125, the platform 144, and the vacuum holes 198.

A control system 200 is coupled in operative control communication with the drive assembly 114 and with vacuum assembly 196 to operate the drive assembly 114 and the vacuum assembly 196 to convey the first and second leg cuffs 156, 158 from the web 102, and to apply the first and second leg cuffs 156, 158 to the absorbent article 20. The control system 200 includes a controller 202 that is coupled to the drive assembly 114, the vacuum assembly 196, and one or more sensors 204. Each sensor 204 senses various parameters relative to the operation of the drive assembly 114, the transfer segments 118, and/or the vacuum assembly 196. The sensors 204 may include, but are not limited to only including, position sensors, angular speed sensors, proximity sensors, and/or any other sensors that sense various parameters relative to the operation of the apparatus 110. The sensors 204 can be any suitable sensors such as, for example, encoders, reed switches, reed sensors, infra-red type sensors, and/or photo-eye sensors. Alternatively, any sensors that enable operation of the apparatus 110, as described herein may be used.

In one embodiment, the controller 202 includes a processor 206 and a memory device 208. The processor 206 includes any suitable programmable circuit which may include one or more systems and microcontrollers, microprocessors, reduced instruction set circuits (RISC), application specific integrated circuits (ASIC), programmable logic circuits (PLC), field programmable gate arrays (FPGA), and any other circuit capable of executing the functions described herein. The above examples are exemplary only, and thus are not intended to limit in any way the definition and/or meaning of the term "processor." Memory device 208 includes a computer readable medium, such as, without limitation, random access memory (RAM), flash memory, a hard disk drive, a solid state drive, a diskette, a flash drive, a compact disc, a digital video disc, and/or any suitable device that enables processor 206 to store, retrieve, and/or execute instructions and/or data.

In one embodiment, the control system 200 is configured to control a position of a rotary valve or vacuum slug (not shown) to selectively apply a vacuum suction to the platform 144 of the transfer puck assembly 126. Specifically, when the puck segment 138 is at the pick-up location 120 adjacent the web 102, the rotary valve permits the vacuum assembly 196 to apply a vacuum suction through the vacuum holes 198 to cause the web 102 to adhere to the platform 144 of the transfer puck assembly 126. When the puck segment 138 is at the application location 122 adjacent the absorbent article 20, the rotary valve cuts off fluid communication between the vacuum assembly 196 and the transfer puck assembly 126 to release the respective first and second leg cuffs 156, 158 from the platform 144 of the transfer puck assembly 126 to enable the transfer puck assembly 126 to release and thereby apply the first and second leg cuffs 156, 158 to the absorbent article 20.

Figure 13:
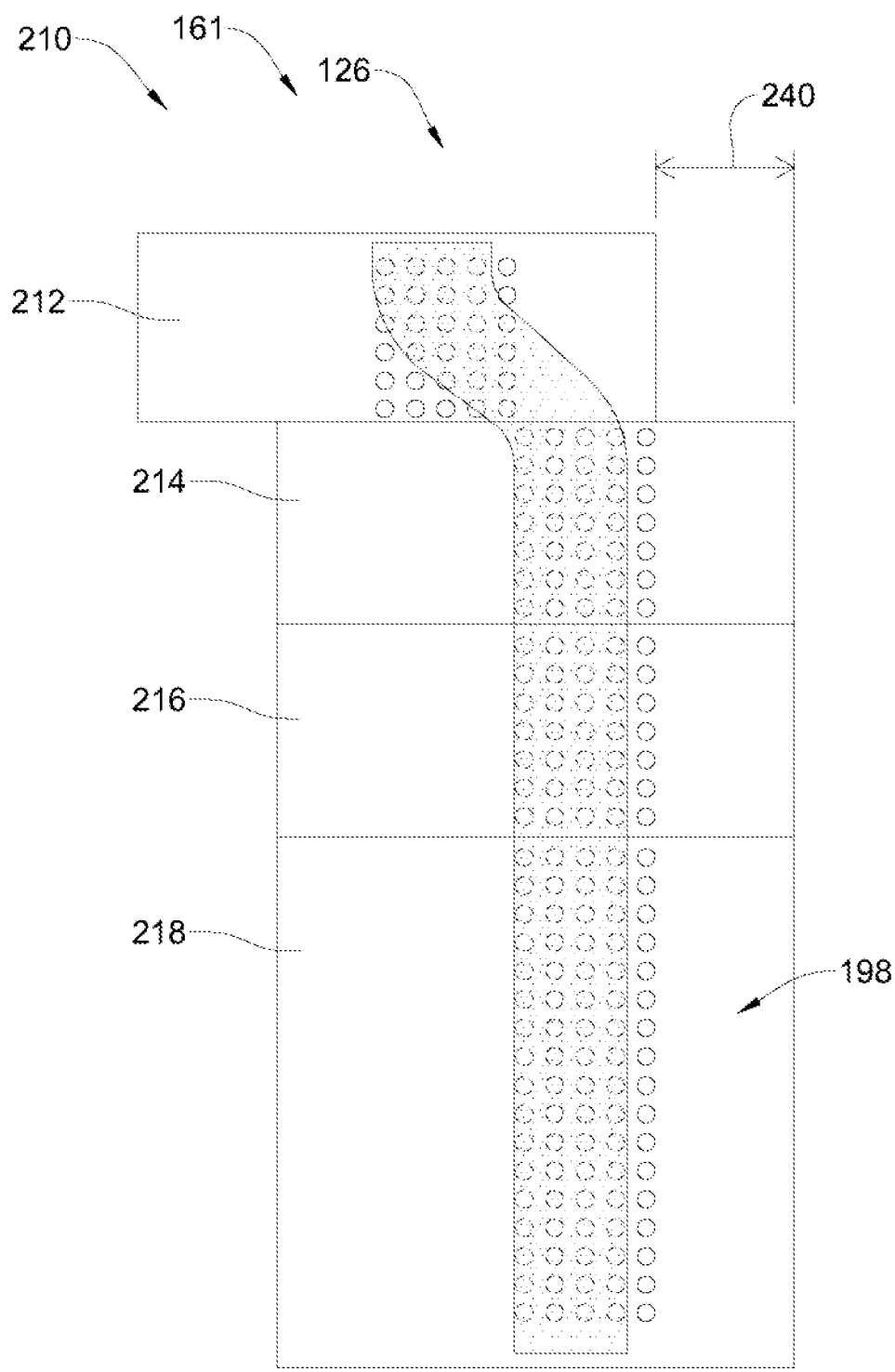
FIG. 13 is a schematic view of the transfer puck assembly illustrated in FIG. 12 including a leg cuff positioned on the transfer puck assembly.
Figure 20:
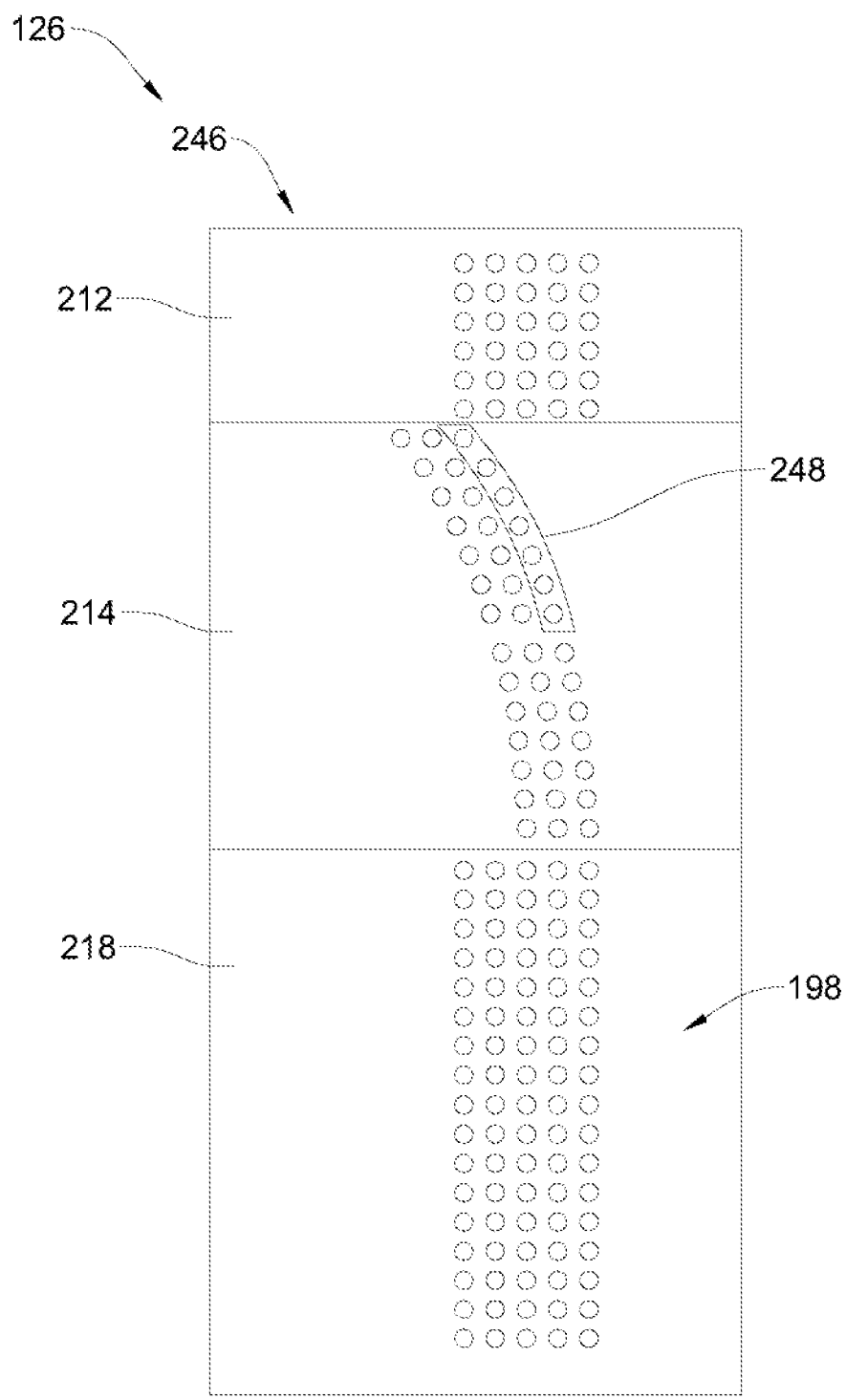
FIG. 20 is a schematic view of the transfer puck assembly illustrated in FIGS. 3 and 4 arranged in a third transfer puck assembly arrangement.
Figure 21:
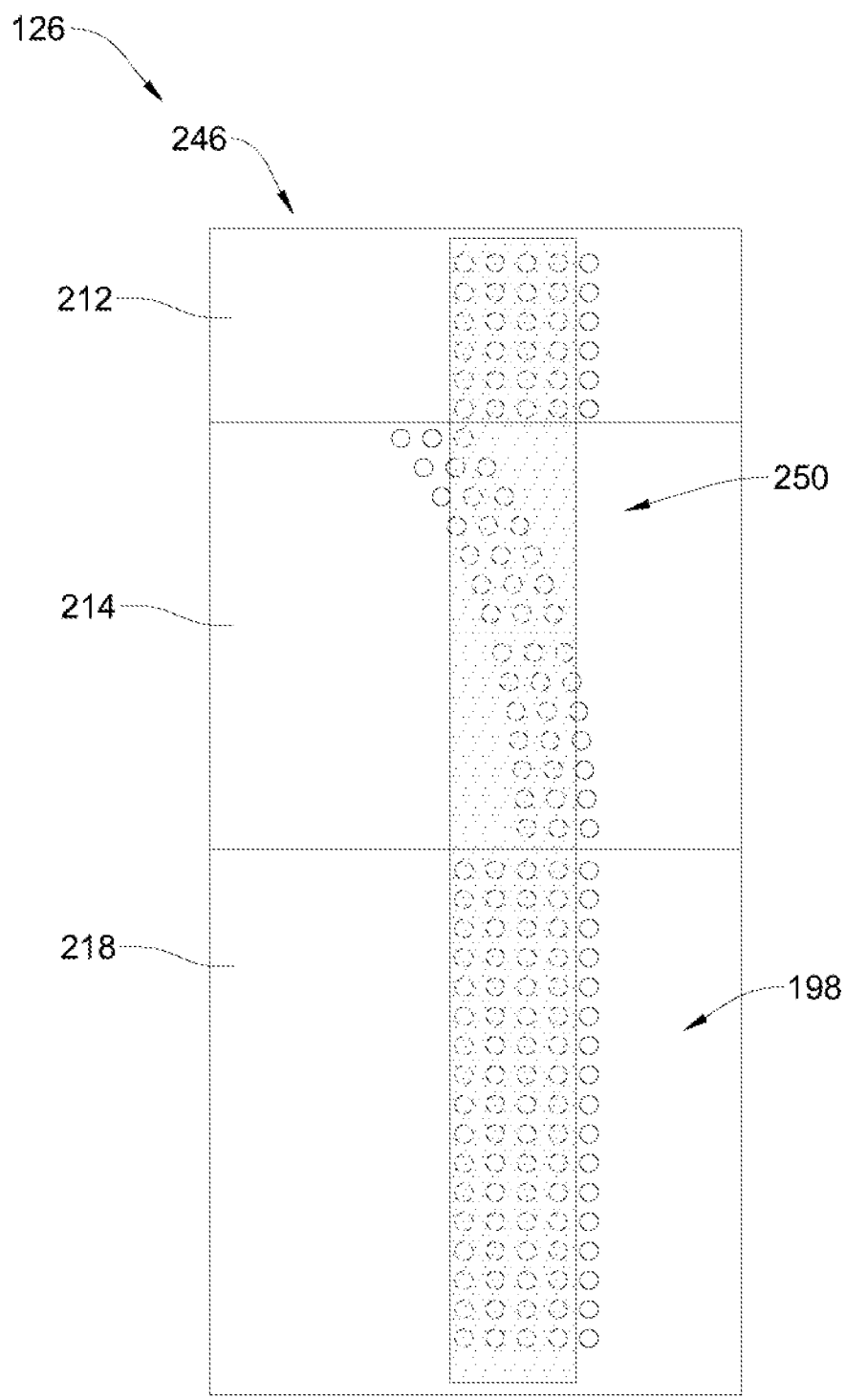
FIG. 21 is a schematic view of the transfer puck assembly illustrated in FIG. 20 including a leg cuff positioned on the transfer puck assembly.
Figure 22:
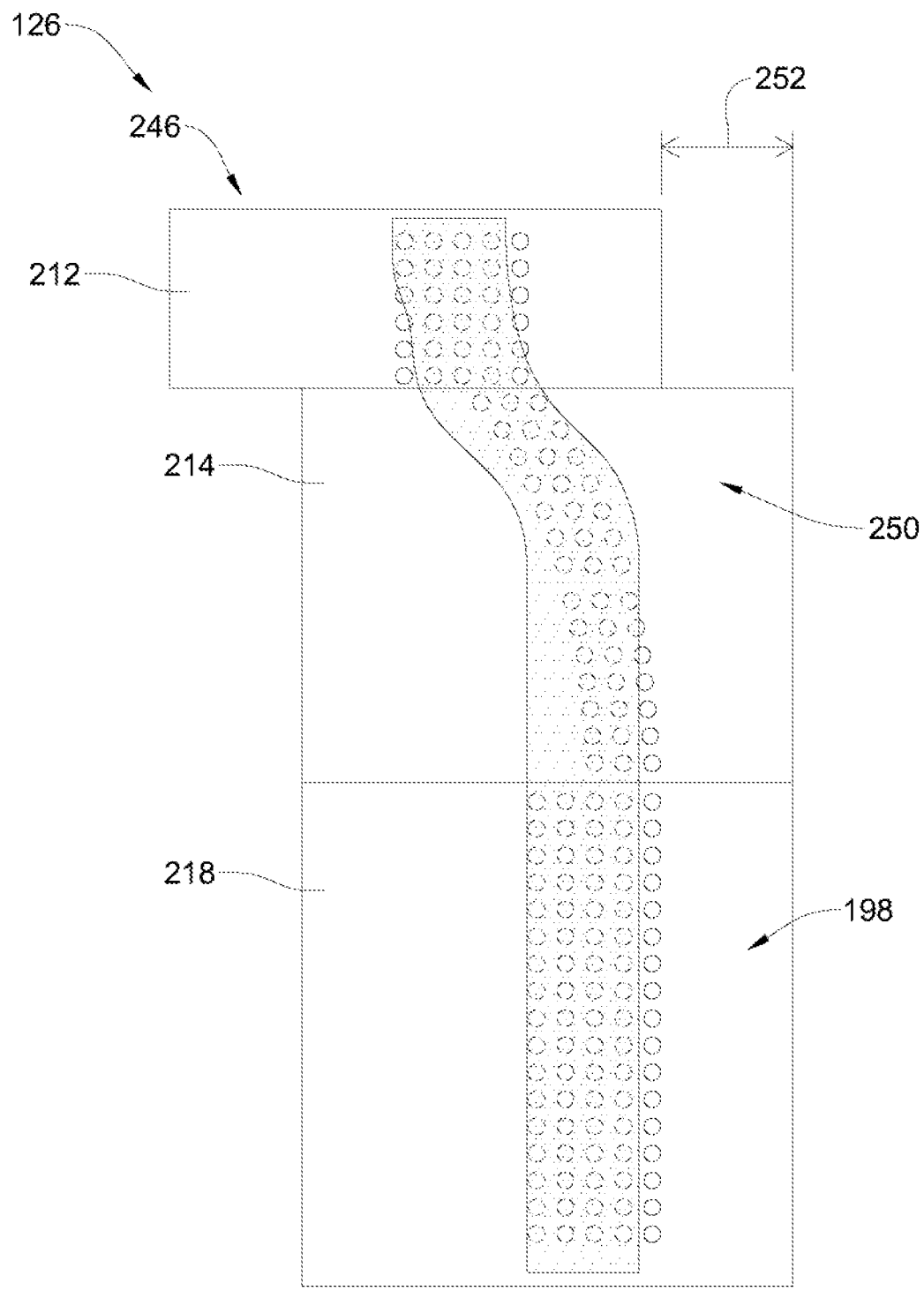
FIG. 22 is a schematic view of the transfer puck assembly illustrated in FIG. 20 with a first puck segment translated from a first position to a second position.

FIGS. 12 and 13 illustrate the first puck assembly 161 of the transfer puck assembly 126 arranged in a first transfer puck assembly arrangement 210. FIGS. 14-18 illustrate the first puck assembly 161 of the transfer puck assembly 126 arranged in a second transfer puck assembly arrangement 254. FIGS. 20-22 illustrate the first puck assembly 161 of the transfer puck assembly 126 arranged in a third transfer puck assembly arrangement 246. As best seen in FIGS. 14-18 illustrating the first puck assembly 161 of the transfer puck assembly 126 arranged in the second transfer puck assembly arrangement 254, the first puck assembly 161 includes a first puck segment 212, a second puck segment 214, a third puck segment 216, and a fourth puck segment or base puck segment 218 arranged such that the transfer puck assembly 126 has a rectangular shape. However, the transfer puck assembly 126 may include any number of puck segments that enable the transfer puck assembly 126 to operate as described herein. Specifically, each puck segment 212-218 has a length 220 and a width 222 and each puck also defines a rectangular shape. In the illustrated embodiment, the width 222 of each puck segment 212-218 is the same, and the length 220 of the first, second, and third puck segments 212-216 are also the same. The length 220 of the fourth puck segment 218 is greater than the length 220 of the first, second, and third puck segments 212-216. More specifically, in this embodiment, the width 222 of each puck segment 212-218 is about 0.25 inches to about 4.0 inches, the length 220 of the fourth puck segment 218 is about 1.0 inches to about 6.0 inches, and the length 220 of the first, second, and third puck segments 212-216 is about 0.25 inches to about 4.0 inches. The radius of curvature R of the first and second leg cuffs 156, 158 is at least partially determined by the length 110 of the puck segments 212-218.

Additionally, each puck segment 212-218 has a first side edge 224, a second side edge 226, a puck leading edge 228, and a puck trailing edge 230. As shown in FIGS. 12-16, the puck segments 212-218 are arranged linearly such that the first puck segment 212 is slidably positioned next to the second puck segment 214, the second puck segment 214 is slidably positioned next to the third puck segment 216, and the third puck segment 216 is slidably positioned next to the fourth puck segment 218. Specifically, the puck trailing edge 230 of the first puck segment 212 is positioned next to the puck leading edge 228 of the second puck segment 214, the puck trailing edge 230 of the second puck segment 214 is positioned next to the puck leading edge 228 of the third puck segment 216, and the puck trailing edge 230 of the third puck segment 216 is positioned next to the puck leading edge 228 of the fourth puck segment 218.

The puck segments 212-218 each include a joint assembly (not shown) that allows the puck segments to slide or translate along axial direction 136 without separating from each other. For example, the joint assembly may include a tongue and groove assembly that enables the puck segments 212-218 to slide or translate along axial direction 136 without separating from each other. Specifically, the puck leading edges 228 of the second, third, and fourth puck segments 214-218 may each include a ridge (not shown), and the puck trailing edges 230 of the first, second, and third puck segments 212-216 may each include a groove or slot (not shown) that has a shape and size that corresponds to a shape and size of the ridges of the first, second, and third puck segments. The ridges of the second, third, and fourth puck segments 214-218 are positioned within the grooves of the first, second, and third puck segments 212-216 and retain a position of the puck segments 212-218 relative to each other in a circumferential direction 232 as the puck segments slide or translate in the axial direction 136. In alternative embodiments, the puck segments 212-218 may include joint assembly that enables the transfer puck assembly 126 to operate as described herein.

In an alternative embodiment illustrated in FIGS. 12 and 13, the first transfer puck assembly arrangement 210 only includes the first puck segment 212 and the second, third, and fourth puck segments 214-218 are combined into a fifth puck 256. In the illustrated embodiment, the length 220 of the fifth puck 256 is equivalent to the combined lengths 220 of the second, third, and fourth puck segments 214-218. As described below, the first and fifth puck segments 212 and 256 operate in manner consistent with the operation of the transfer puck assembly 126 illustrated in FIGS. 12-16.

As described above, the puck segments 212-218 each define vacuum holes 198 fluidly connected to the vacuum assembly 196, and the vacuum assembly 196 selectively applies a vacuum suction through the vacuum holes 198, retaining the leg cuffs 62 on the transfer puck assembly 126. The vacuum holes 198 each define a vacuum hole diameter 234 and are arranged in rows 236 and columns 238. In the second transfer puck assembly arrangement 254, each puck segment 212-218 includes five columns 238 of vacuum holes 198, the fourth puck segment 218 includes 17 rows 236 of vacuum holes 198, the second and third puck segments 214 and 216 each include seven rows 236 of vacuum holes 198, and the first puck segment 212 includes six rows 236 of vacuum holes 198. In alternative embodiments, the puck segments 212-218 may each include any number of rows 236 and columns 238 of vacuum holes 198 that enable the transfer puck assembly 126 to operate as described herein. In the first transfer puck assembly arrangement 210 illustrated in FIG. 12, the first puck segment 212 includes six rows 236 of vacuum holes 198, and the fifth puck 256 includes 31 rows 236 of vacuum holes 198. Additionally, in the second transfer puck assembly arrangement 254, the vacuum hole diameters 234 of each of the vacuum holes 198 are the same. In alternative embodiments, the vacuum hole diameters 234 of each of the vacuum holes 198 are different. In the illustrated embodiment, the vacuum hole diameter 234 of each of the vacuum holes 198 is about 0.06 inches to about 0.15 inches. In alternative embodiments, the vacuum hole diameter 234 of each of the vacuum holes 198 may be any size that enables the transfer puck assembly 126 to operate as described herein.

Figure 14:
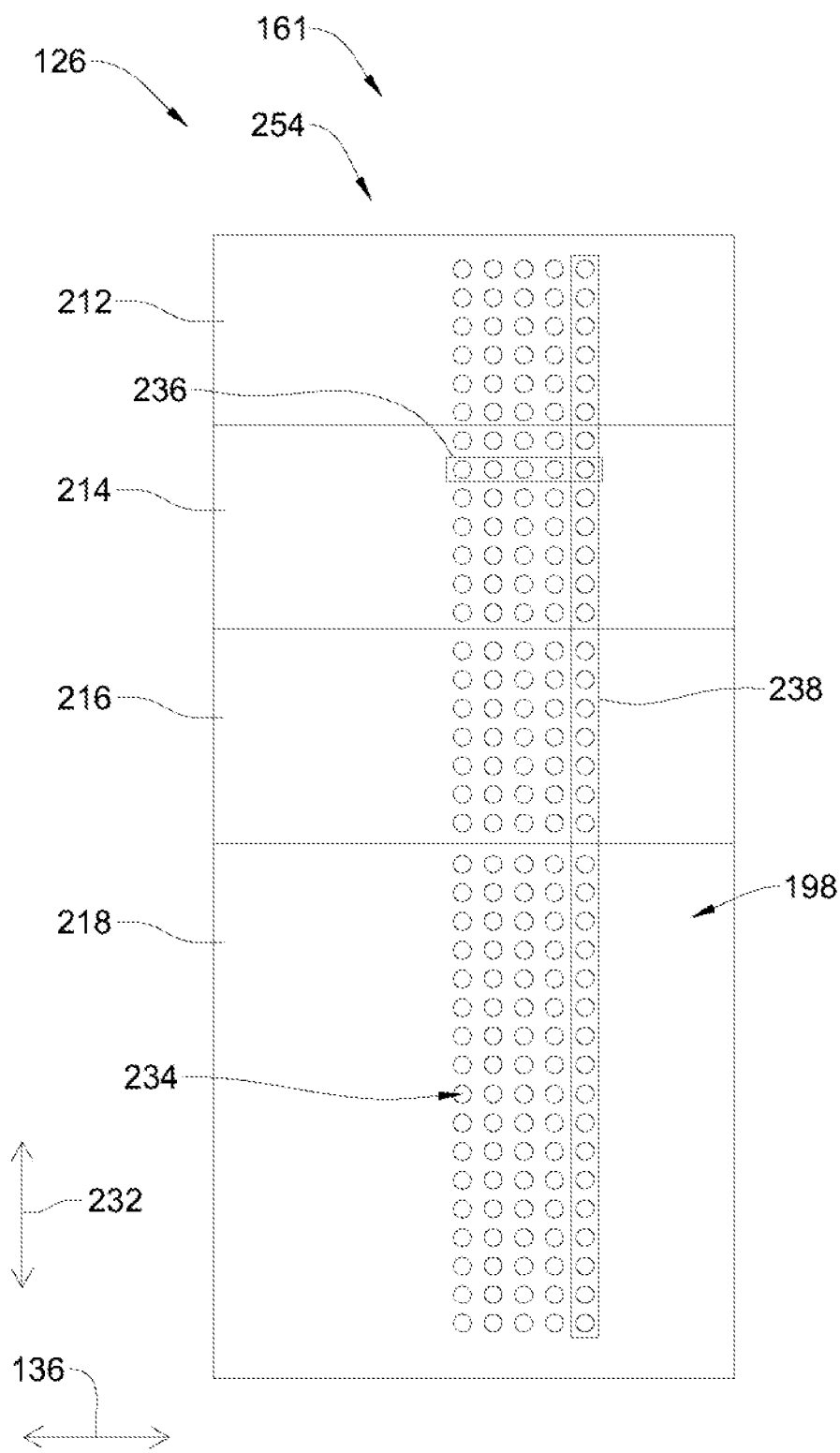
FIG. 14 is a schematic view of the transfer puck assembly illustrated in FIG. 13 with a first puck segment translated from a first position to a second position.
Figure 15:
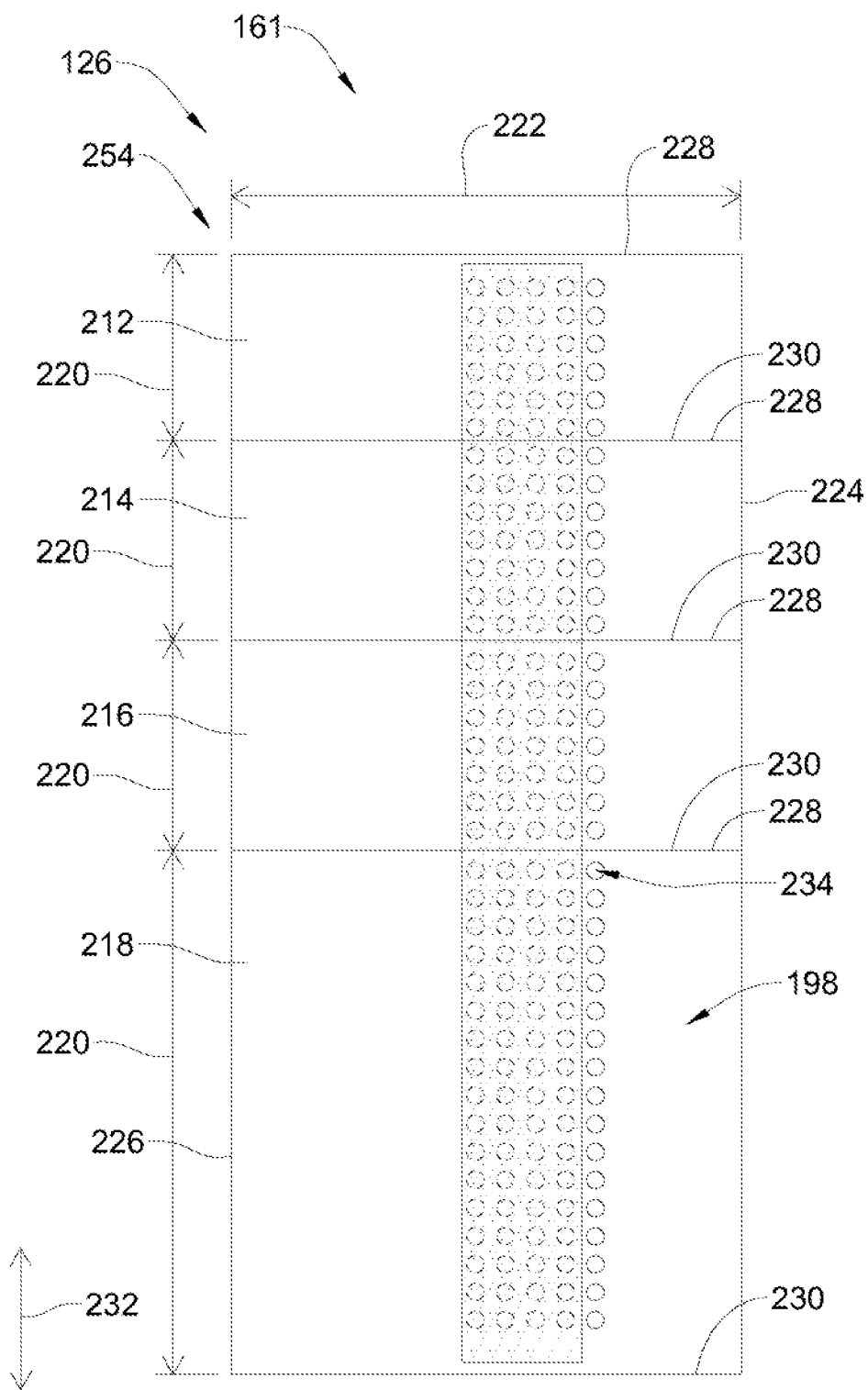
FIG. 15 is a schematic view of the transfer puck assembly illustrated in FIG. 13 with a first puck segment and a second puck segment translated from a first position to a second position.

As shown in FIGS. 14 and 15, in the second transfer puck assembly arrangement 254, when the transfer puck assembly 126 is in the first position 148, oriented to receive the leg cuffs 62 at the pick-up location 120, the puck segments 212-218 are arranged such that the transfer puck assembly has a rectangular shape. Specifically, in the first position 148, the puck segments 212-218 are arranged such that the first side edges 224 of the puck segments are aligned, and the second side edges 226 of the puck segments are aligned, forming the rectangular shape of the transfer puck assembly 126. Additionally, the columns 238 of vacuum holes 198 of each puck segment 212-218 are aligned in a linear arrangement. In the first transfer puck assembly arrangement 210 illustrated in FIG. 12, the first puck segment 212 is aligned with the fifth puck 256 such that the first transfer puck assembly arrangement has a rectangular shape similar to the linear arrangement of the transfer puck assembly 126 illustrated in FIG. 14.

Figure 16:
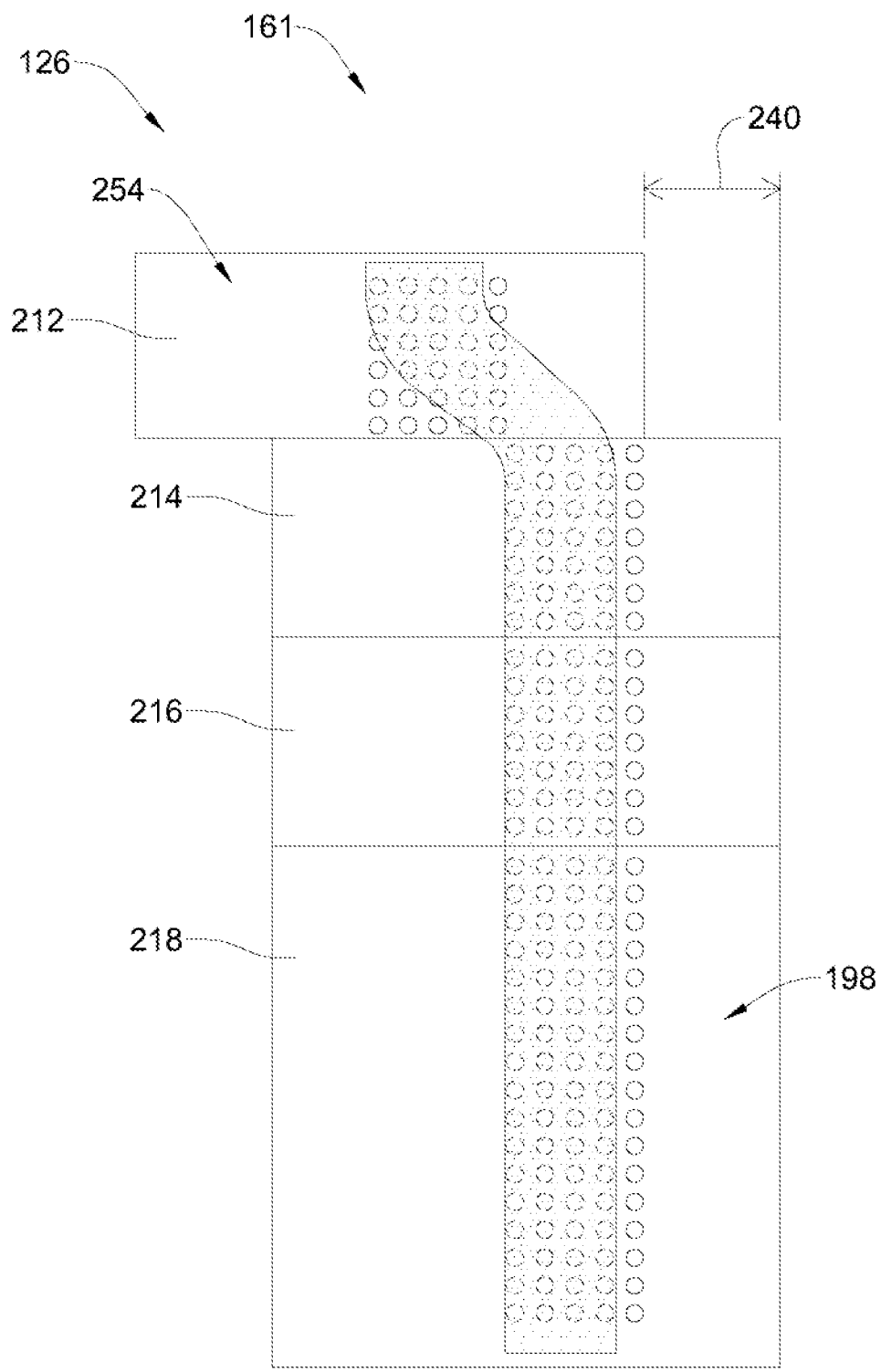
FIG. 16 is a schematic view of the transfer puck assembly illustrated in FIG. 13 with a first puck segment, a second puck segment, and a third puck segment translated from a first position to a second position.
Figure 17:
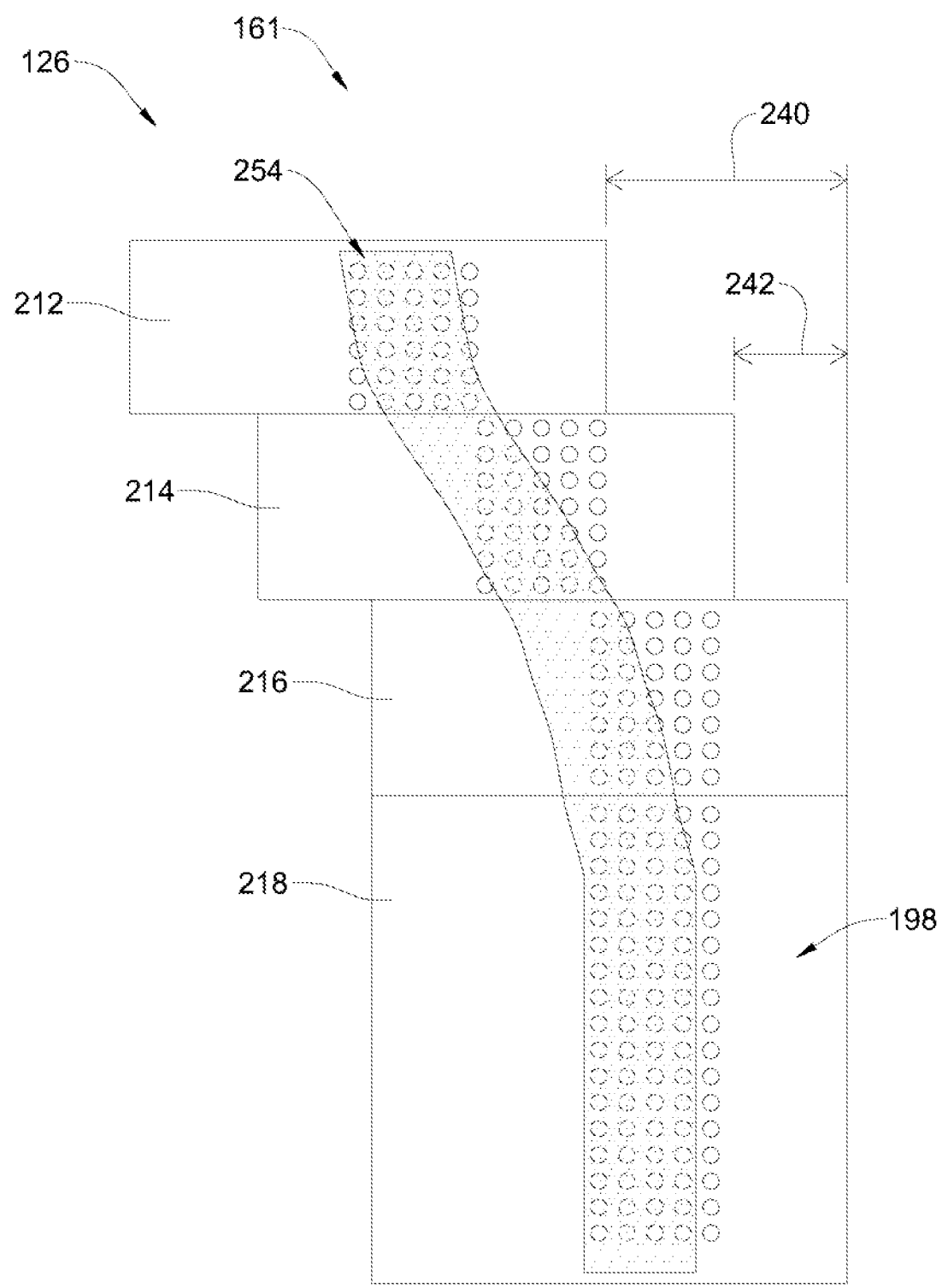
FIG. 17 is a schematic view of the transfer puck assembly illustrated in FIGS. 3-5 arranged in a second transfer puck assembly arrangement.
Figure 18:
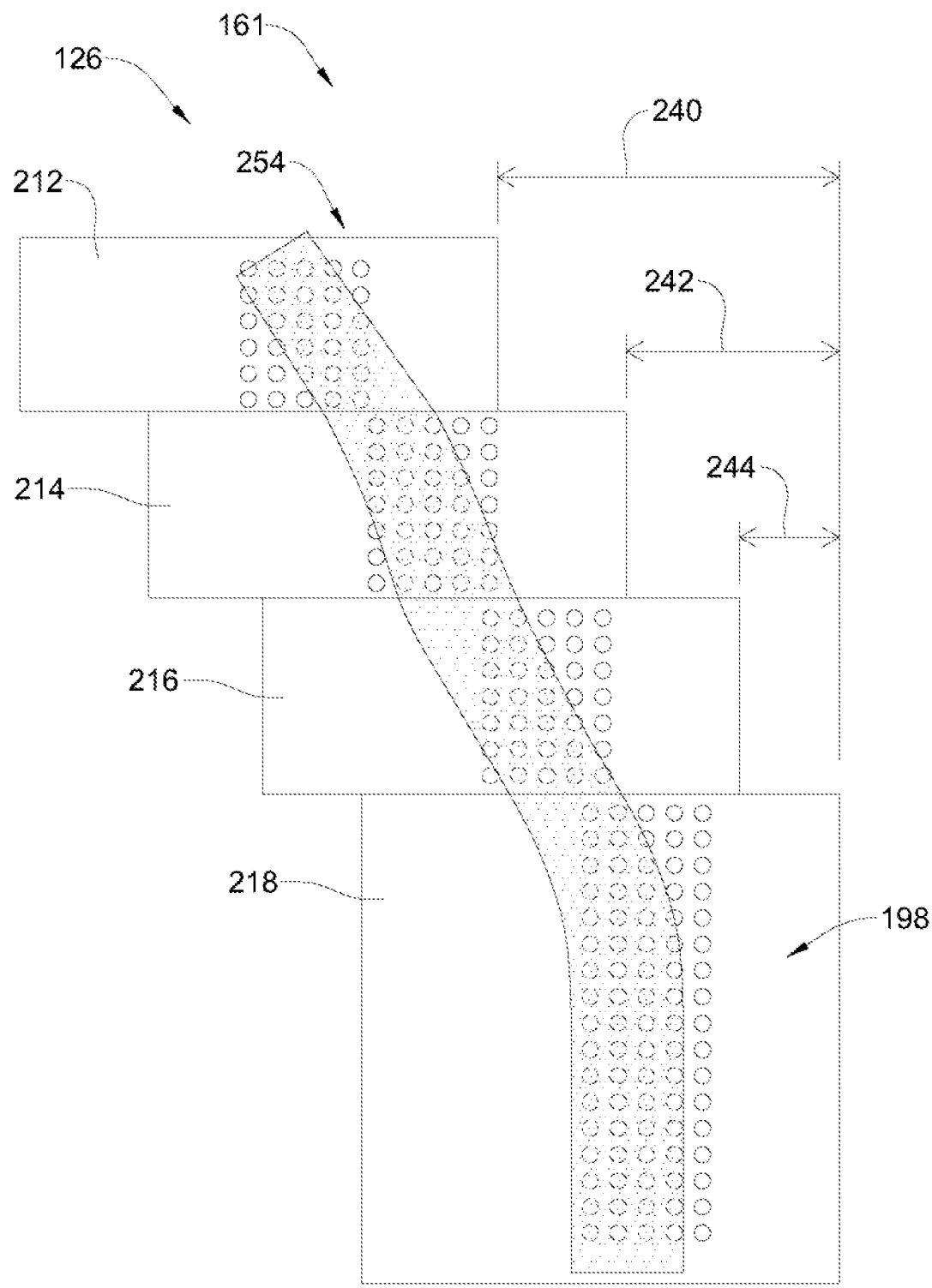
FIG. 18 is a schematic view of the transfer puck assembly illustrated in FIG. 17 with a first puck segment translated from a first position to a second position.

As shown in FIGS. 16, 17, and 18, in the second transfer puck assembly arrangement 254, when the transfer puck assembly 126 is in the second position 150, oriented to apply the leg cuffs 62 to the absorbent article 20 at the application location 122, one or more of the first, second, and third puck segments 212-216 are translated in the axial direction 136 to curve the leg cuffs 62 prior to applying the leg cuffs 62 to the absorbent article 20. In the embodiment illustrated in FIG. 14, only the first puck segment 212 is translated in the axial direction 136. In the embodiments illustrated in FIGS. 15 and 16, the first and second puck segments 212 and 214 and the first, second, and third puck segments 212-216 are translated in the axial direction 136, respectively.

Similarly, the first transfer puck assembly arrangement 210 illustrated in FIGS. 12 and 13, the transfer puck assembly 126 is in the second position 150, oriented to apply the leg cuffs 62 to the absorbent article 20 at the application location 122, the first puck segment 212 is translated relative to the fifth puck 256 in the axial direction 136 to curve the leg cuffs 62 prior to applying the leg cuffs 62 to the absorbent article 20.

Specifically, in the embodiment illustrated in FIG. 14, only the first puck segment 212 is translated a first translation distance 240 in the axial direction 136 to curve the leg cuffs 62 prior to applying the leg cuffs 62 to the absorbent article 20. In the illustrated embodiment, the first translation distance 240 is about 0.5 inches to about 2.0 inches. In alternative embodiments, the first translation distance 240 may be any distance that enables the transfer puck assembly 126 to operate as described herein.

In the embodiment illustrated in FIG. 16, the first puck segment 212 is translated the first translation distance 240 in the axial direction 136 and the second puck segment 214 is translated a second translation distance 242 to curve the leg cuffs 62 prior to applying the leg cuffs 62 to the absorbent article 20. In the illustrated embodiment, the first translation distance 240 is about 0.5 inches to about 2.0 inches, and the second translation distance 242 is about 0.25 inches to about 1.0 inches. Specifically, the first translation distance 240 is greater than the second translation distance 242. In alternative embodiments, the first translation distance 240 and the second translation distance 242 may be any distance that enables the transfer puck assembly 126 to operate as described herein.

In the embodiment illustrated in FIG. 18, the first puck segment 212 is translated the first translation distance 240 in the axial direction 136, the second puck segment 214 is translated a second translation distance 242, and the third puck segment 216 is translated a third translation distance 244 to curve the leg cuffs 62 prior to applying the leg cuffs 62 to the absorbent article 20. In the illustrated embodiment, the first translation distance 240 is about 0.75 inches to about 3.0 inches, the second translation distance 242 is about 0.5 inches to about 2.0 inches, and the third translation distance 244 is about 0.25 inches to about 1.0 inches. Specifically, the first translation distance 240 is greater than the second translation distance 242 and the third translation distance 244, and the second translation distance 242 is greater than the third translation distance 244. In alternative embodiments, the first, second, and third translation distances 240-244 may be any distance that enables the transfer puck assembly 126 to operate as described herein.

Figures 19A, 19B:
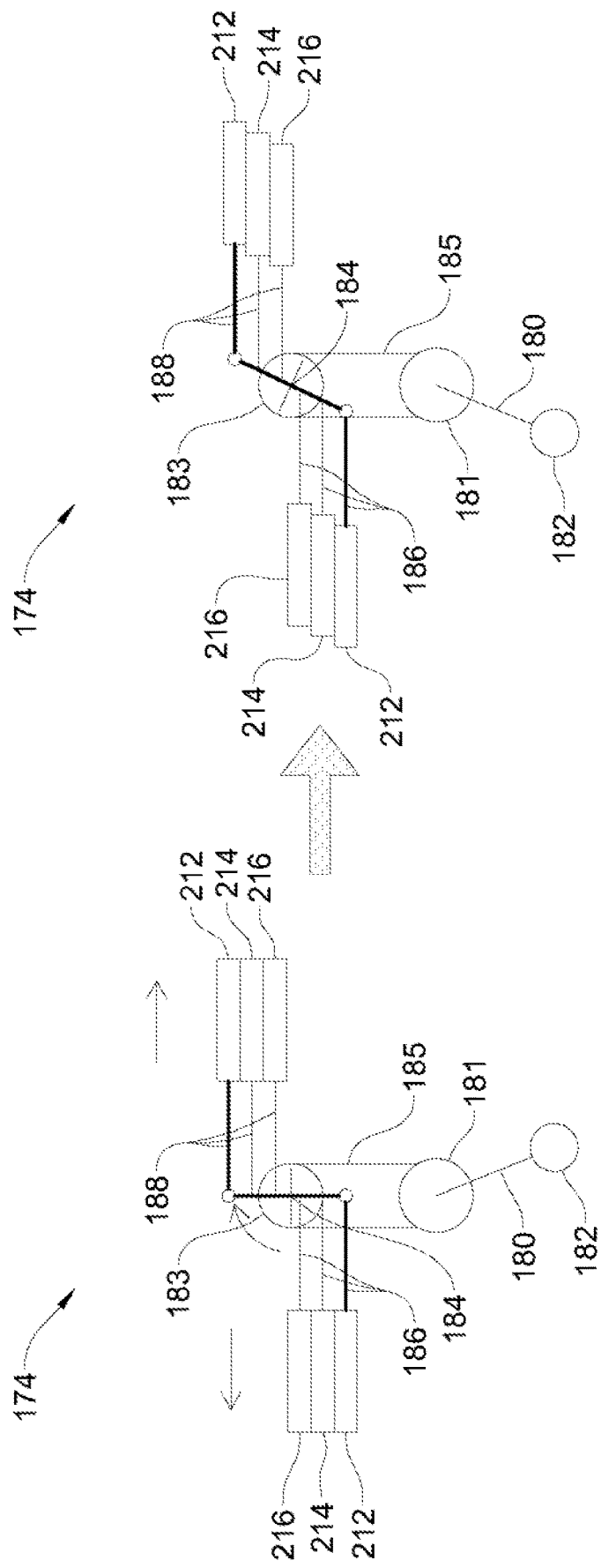
FIG. 19A is a schematic view of another embodiment of the follower and the linkage assembly illustrated in FIGS. 6A and 6B in a first position.
FIG. 19B is a schematic view of the follower and the linkage assembly illustrated in FIG. 19A moved to a second position.

As described above, the barrel cam 174 is coupled to each transfer puck assembly 126 to translate at least one of first, second, and third puck segments 212-216 of each transfer puck assembly 126 along the axial direction 136. More specifically, as illustrated in FIGS. 19A and 19B, the apparatus 110 includes a plurality of first translation segments 186 associated with the first, second, and third puck segments 212-216 of the first translating puck segment 162 and a plurality of second translation segments 188 associated with the first, second, and third puck segments 212-216 of the second translating puck segment 164. The cam follower 182 rotates the cam arm 180 about the pivot point 184 as each transfer puck assembly 126 rotates about the drive axis 116. The cam arm 180 translates the first and second translation segments 186 and 188 and at least one of second, third, and fourth puck segments 214-218 along the axial direction 136.

As best seen in FIGS. 20-22 illustrating one side of the transfer puck assembly 126 arranged in the third transfer puck assembly arrangement 246, the transfer puck assembly 126 includes the first, second, and fourth puck segments 212, 214, and 218. Additionally, while the first and fourth puck segments 212 and 218 each include vacuum holes 198 arranged in rows 236 and columns 238 similar to the first and fourth puck segments 212 and 218 of the second transfer puck assembly arrangement 254, the second puck segment 214 includes vacuum holes 198 arranged in rows 236 and curved columns 248. More specifically, in the third transfer puck assembly arrangement 246, the second puck segment 214 includes seven rows 236 of vacuum holes 198 and three curved columns 248 of vacuum holes 198 at least partially misaligned with the columns 238 of vacuum holes 198 of the first and fourth puck segments 212 and 218.

As shown in FIGS. 20 and 21, in the third transfer puck assembly arrangement 246, when the transfer puck assembly 126 is in the first position 148, oriented to receive the leg cuffs 62 at the pick-up location 120, the puck segments 212, 214, and 218 are arranged in a linear arrangement similar to the linear arrangement of the second transfer puck assembly arrangement 254. Specifically, the columns 238 of vacuum holes 198 of the first and fourth puck segments 212 and 218 are aligned in a linear arrangement, but the curvature of the curved columns 248 causes the curved columns 248 of vacuum holes 198 of the second puck segment 214 to be at least partially misaligned with the columns 238 of vacuum holes 198 of the first and fourth puck segments 212 and 218.

As shown in FIG. 21, in the third transfer puck assembly arrangement 246, when the transfer puck assembly 126 is in the second position 150, oriented to apply the leg cuffs 62 to the absorbent article 20 at the application location 122, only the first puck segment 212 is translated in the axial direction 136 to curve the leg cuffs 62 prior to applying the leg cuffs 62 to the absorbent article 20. Specifically, only the first puck segment 212 is translated a fourth translation distance 252 causing a portion 250 of the leg cuff 62 covering the second puck segment. 214 to also translate in the axial direction 136. Translation of the portion 250 of the leg cuff 62 covering the second puck segment 214 causes the leg cuff 62 to assume a curved shape corresponding to the curvature of the curved columns 248 of the second puck segment 214. In the illustrated embodiment, the fourth translation distance 252 is about 0.5 inches to about 2.0 inches. In alternative embodiments, the fourth translation distance 252 may be any distance that enables the transfer puck assembly 126 to operate as described herein. The curved hole pattern of the curved columns 248 of the second puck segment 214 reduces friction and enables the radius of curvature R of the first and second leg cuffs 156, 158 to be controlled. Accordingly, the curvature of the curved columns 248 of the third transfer puck assembly arrangement 246 enables the transfer puck assembly 126 to control the radius of curvature R of the first and second leg cuffs 156, 158 and reduces friction between the first and second leg cuffs 156, 158 and the puck segments 212, 214, and 218.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for conveying and applying a discrete part to a substrate, the apparatus comprising:
    a plurality of transfer puck assemblies adapted to convey the discrete part to the substrate, each transfer puck assembly including at least one puck segment;
    a drive assembly configured to rotate each transfer puck assembly about a drive axis; and
    a translation mechanism configured to translate the at least one puck segment in an axial direction as the plurality of transfer puck assemblies are being rotated about the drive axis to move the discrete part to a profiled configuration prior to application of the discrete part to the substrate.

2. The apparatus as set forth in claim 1, wherein the at least one puck segment is translatable between a first position wherein the transfer puck assembly is oriented to receive the discrete part, and a second position wherein the transfer puck assembly is oriented to apply the discrete part to the substrate.

3. The apparatus as set forth in claim 2, further comprising a plurality of transfer segments, each of the transfer segments comprising one of the plurality of transfer puck assemblies, wherein the plurality of transfer puck assemblies includes a first transfer puck assembly and a second transfer puck assembly, the drive assembly being configured to rotate the first transfer puck assembly and the second transfer puck assembly about drive axis such that the first transfer puck assembly separates from the second transfer puck assembly and the discrete part conveyed on the first transfer puck assembly is separated from the discrete part conveyed on the second transfer puck assembly.

4. The apparatus as set forth in claim 2, further comprising a perforator for at least partially perforating the web.

5. The apparatus as set forth in claim 2, further comprising an applicator for applying an adhesive to the web.

6. The apparatus as set forth in claim 3, wherein the drive assembly comprises a translation mechanism, each transfer segment of the plurality of transfer segments comprises:
    a cam arm extending; and
    a cam follower adapted to engage the translation mechanism and the cam arm to selectively translate the at least one puck segment in the axial direction.

7. The apparatus as set forth in claim 6, each transfer segment of the plurality of transfer segments further comprises a translation segment coupled to the cam arm and the at least one puck segment, wherein rotation of the cam arm translates the translation segment, and translation of the translation segment translates the at least one puck segment in the axial direction.

8. The apparatus as set forth in claim 2, further comprising a vacuum assembly coupled to the transfer puck assemblies, the vacuum assembly configured to selectively apply a vacuum to the transfer puck assemblies to facilitate conveying each discrete part from the web to the substrate.

9. The apparatus as set forth in claim 1, wherein the plurality of transfer puck assemblies are each configured to apply a pair of discrete parts of the substrate.

10. The apparatus as set forth in claim 1, wherein the discrete parts are leg cuffs including an elastic material.

11. Apparatus for conveying a discrete part and applying the discrete part to a substrate, the apparatus comprising:
    a plurality of transfer puck assemblies adapted to convey the plurality of discrete parts to the substrate, each transfer puck assembly including a first puck segment and a second puck segment;
    a drive assembly configured to rotate each transfer puck assembly about a drive axis; and
    a translation mechanism configured to translate at least one of the first and second puck segments in an axial direction as the plurality of transfer puck assemblies are rotated about the drive axis to profile the discrete part prior to application of the profiled discrete part to the substrate.

12. The apparatus as set forth in claim 11, wherein the first puck segment is translated a first translation distance in the axial direction.

13. The apparatus as set forth in claim 11, wherein each transfer puck assembly further includes a third puck segment, and wherein the first puck segment is translated a first translation distance in the axial direction and the second puck segment is translated a second translation distance in the axial direction, the first translation distance being greater than the second translation distance.

14. The apparatus as set forth in claim 13, wherein each transfer puck assembly further includes a fourth puck segment, and wherein the first puck segment is translated a first translation distance in the axial direction, the second puck segment is translated a second translation distance in the axial direction, and the third puck segment is translated a third translation distance in the axial direction, the first translation distance and the third translation distance, and the second translation distance being greater than the third translation distance.

15. The apparatus as set forth in claim 11, wherein each of the first and second puck segments comprises a plurality of vacuum holes, the apparatus further comprising a vacuum assembly in fluid communication with each of the vacuum holes to selectively apply a vacuum.

16. The apparatus as set forth in claim 15, wherein the vacuum holes of the first and second segments are arranged in a plurality of rows and columns, wherein the columns of vacuum holes of the first and second puck segments are aligned.

17. The apparatus as set forth in claim 15, wherein the vacuum holes of the first and second puck segments are arranged in a plurality of rows, the vacuum holes of the first puck segment are arranged in a plurality of columns, and at least some of the vacuum holes of the second puck segment are arranged in a plurality of curved columns.

18. A method of applying discrete parts to a substrate comprising:

feeding a plurality of discrete parts towards a plurality of transfer puck assemblies rotatably coupled to a drive assembly, each transfer puck assembly including at least one puck segment;

receiving a discrete part of the plurality of discrete parts onto each of the transfer puck assemblies;

rotating each transfer puck assembly such that each transfer puck assembly conveys each discrete part to the substrate;

simultaneously translating the at least one puck segment in an axial direction to profile the discrete part of the plurality of discrete parts; and applying the discrete part of the plurality of discrete parts to the substrate such that the applied discrete part of the plurality of discrete parts has a profiled configuration.

19. The method of claim 18, wherein translating the at least one puck segment in an axial direction to profile the discrete part of the plurality of discrete parts comprises translating the at least one puck segment from a first position, where the transfer puck assembly is oriented to receive the discrete part of the plurality of discrete parts from the web, to a second position, where the transfer puck assembly is oriented to apply the discrete part of the plurality of discrete parts to the substrate.

20. The method of claim 18, further comprising:

accelerating each transfer puck assembly such that a speed of the transfer puck assembly is approximately equal to a speed of the substrate as the discrete part of the plurality of discrete parts is applied to the substrate by the transfer puck assembly at an application location.

* * * * *